US010565660B2

(12) United States Patent
Levy

(10) Patent No.: US 10,565,660 B2
(45) Date of Patent: Feb. 18, 2020

(54) MEDICAL CLAIM DATABASE RELATIONSHIP PROCESSING

(71) Applicant: SUNBELT MEDICAL MANAGEMENT, LLC, Tucson, AZ (US)

(72) Inventor: Yoram S. Levy, Tucson, AZ (US)

(73) Assignee: SUNBELT MEDICAL MANAGEMENT, LLC, Tucson, AZ (US)

( * ) Notice: Subject to any disclaimer, the term of this patent is extended or adjusted under 35 U.S.C. 154(b) by 0 days.

(21) Appl. No.: 16/270,346

(22) Filed: Feb. 7, 2019

(65) Prior Publication Data

US 2019/0244302 A1 Aug. 8, 2019

Related U.S. Application Data

(60) Provisional application No. 62/627,483, filed on Feb. 7, 2018.

(51) Int. Cl.
| | |
|---|---|
| *G06Q 40/08* | (2012.01) |
| *G16H 10/60* | (2018.01) |
| *G16H 40/20* | (2018.01) |
| *G06Q 10/10* | (2012.01) |

(52) U.S. Cl.
CPC ............ *G06Q 40/08* (2013.01); *G16H 10/60* (2018.01); *G06Q 10/10* (2013.01); *G16H 40/20* (2018.01)

(58) Field of Classification Search
None
See application file for complete search history.

(56) References Cited

U.S. PATENT DOCUMENTS

| | | | | | |
|---|---|---|---|---|---|
| 5,991,733 | A  * | 11/1999 | Aleia | ............... | G06Q 10/06311 705/7.13 |
| 6,879,959 | B1 * | 4/2005 | Chapman | ............... | G06Q 10/10 705/2 |
| 8,095,391 | B2 * | 1/2012 | Obora | ................... | G06Q 40/08 705/1.1 |
| 8,280,792 | B2 * | 10/2012 | Rajan | .................... | G06Q 20/10 705/34 |

(Continued)

OTHER PUBLICATIONS

International Search Report and Written Opinion issued in application No. PCT/US19/17082, dated Apr. 23, 2019 (10 pgs).

*Primary Examiner* — Michael Tomaszewski
(74) *Attorney, Agent, or Firm* — Hayes Soloway P.C.

(57) ABSTRACT

A method for processing relationships in a medical claims database using a computerized system having a processor and a non-transitory memory includes storing multi-field medical claim data and multi-field insurance claim data in a relational electronic database. The insurance claim data corresponds to at least a portion of the medical claim data. A worklist template is defined using at least one filter and at least one multiplier. The at least one filter excludes at least a portion of the medical claim data, and the at least one multiplier defines a weighted value applicable to at least one field of the multi-field medical claim data. The processor converts the medical claim data into standardized values by applying the at least one multiplier to at least one field of the multi-field medical claim data. A biller worklist is assigned based on a hierarchy of the standardized values.

20 Claims, 28 Drawing Sheets

(56) References Cited

U.S. PATENT DOCUMENTS

| | | | |
|---|---|---|---|
| 2002/0087342 A1* | 7/2002 | Garvey | G06Q 20/102 |
| | | | 705/40 |
| 2005/0187872 A1* | 8/2005 | Schmidt | G06Q 20/102 |
| | | | 705/40 |
| 2007/0011030 A1* | 1/2007 | Bregante | G06F 19/328 |
| | | | 705/4 |
| 2011/0202370 A1 | 8/2011 | Green, III et al. | 705/3 |
| 2012/0029946 A1* | 2/2012 | Aquila | G06Q 40/02 |
| | | | 705/4 |
| 2012/0123807 A1* | 5/2012 | Seaver | G06Q 40/08 |
| | | | 705/4 |
| 2015/0186821 A1 | 7/2015 | Wang et al. | G06Q 10/0639 |
| 2016/0247235 A1 | 8/2016 | Dinamani et al. | G06Q 40/08 |
| 2017/0220998 A1 | 8/2017 | Horn et al. | G06Q 10/10 |

\* cited by examiner

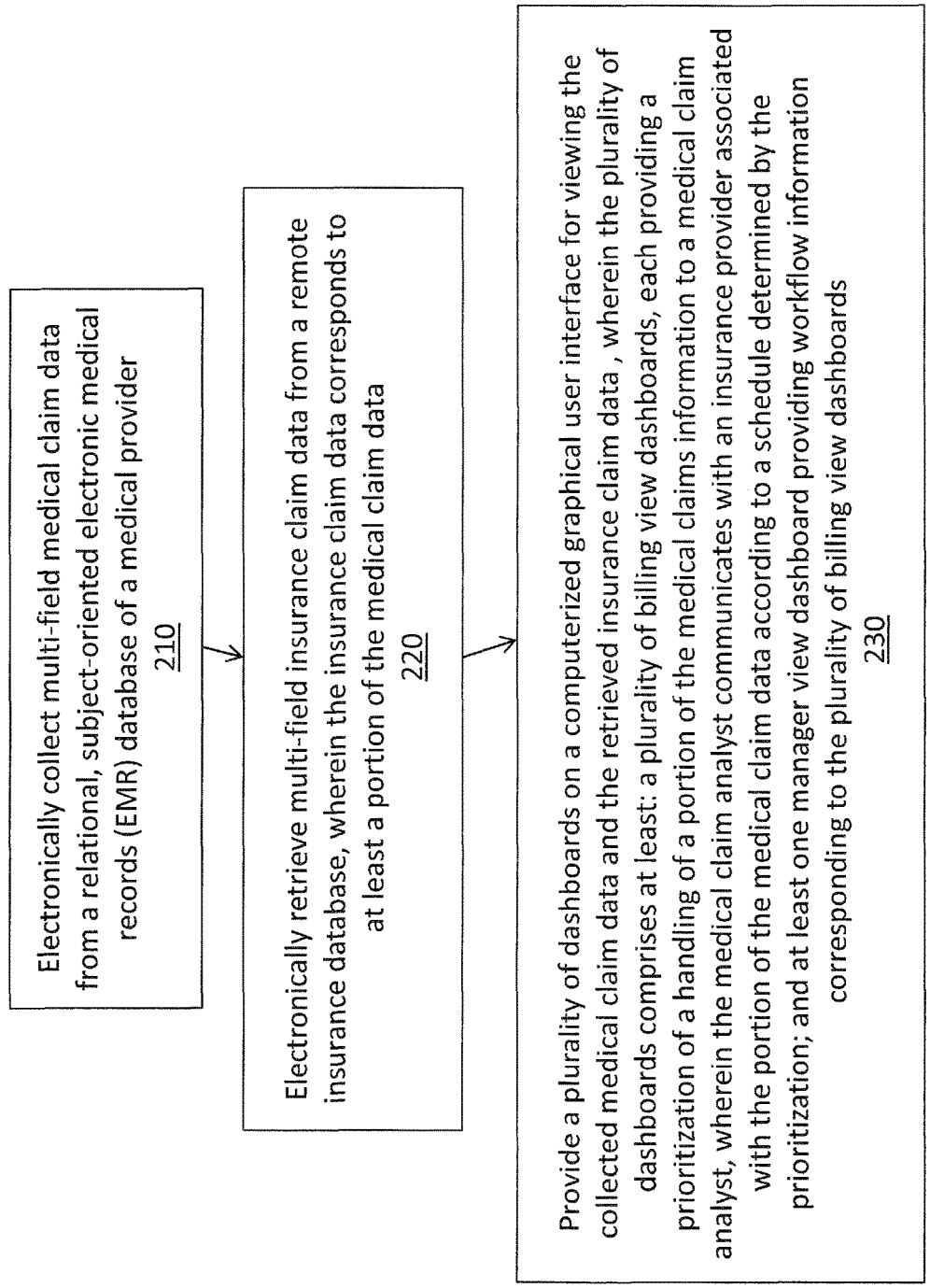

Worked Claims

Filters

Date Worked: [mm/dd/yyyy] - [mm/dd/yyyy]  Client: [Select Some Options]  Action Code: [Select Some Options]
Claim Number: [            ]  Action: [Select Some Options]  Skip Reason: [Select Some Options]
Patient Number: [            ]

[Apply Filters] [Reset Filters] [Set As Default] [Load Default]

HOME>ASSIGN BY BILLER

500 NOTES

Download As: .csv, .xls

| Claim | Client | Patient | Date Worked | Action | Action code | Note | Actions |
|---|---|---|---|---|---|---|---|
| 430738 | Client 1 | Patient 1 | 01-08-19 9:43 AM | Note | qwrasd | asd | ⊕ |
| 427759 | Client 2 | Patient 2 | 01-08-19 9:43 AM | Note | qwrasd | asd | ⊕ |
| 429064 | Client 3 | Patient 3 | 01-08-19 9:43 AM | Note | qwrasd | asd | ⊕ |
| 384008 | Client 4 | Patient 4 | 01-14-19 11:04 AM | Note | qwrasd | asdasd | ⊕ |
| 384008 | Client 5 | Patient 5 | 01-14-19 11:04 AM | Note | qwrasd | asdasd | ⊕ |

↙ 710

THE BILLINGTOOL

DASHBOARD

WORKLISTS
Assign by Client
Assign by Biller

CLAIMS CENTER
Claims History
All Claims
Upload Claims
EClinical
Upload

CONFIGURATION
Worklist
Templates
Skip
Reasons
Action Codes
Client
Divisions
Manage
Clients
Manage Biller
Dashboard
Manage Users

ACCOUNT
Change
Password
Log Out

Management > Teams

Search  11/16/2017 1:00:33 PM  Fabian De La Pena

Teams

| # | Name | Manager | Creation Date | Actions |
|---|------|---------|---------------|---------|
| 1 | Clinicient | Lisa Vincent | 9/8/2017 | ▶ |
| 2 | Sunbelt | Lisa Vincent | 9/8/2017 | ▶ |

The Billing Tool Logo
- Dashboard
- Management
- Forum
- Technical Support
- Submit Ticket
- Actions
- Add Team

1110

Manage Clients

1200

Filters

Client Division: [Select Some Options] | Client: [Select Some Options]

[Apply Filters] [Reset Filters] [Set As Default] [Load Default]

Client Name: [Select an Option ▼]
Client Division: [Create New Client]

276 CLIENTS

Download As: .csv

| Client | Division | Created | Last Upload | Last Worked | By | Claims | Manage Client |
|---|---|---|---|---|---|---|---|
| Client 1 | test3456 | 10-05-18 | 01-05-19 2:22 PM | — | — | 0 | ✏️ 📄 |
| Client 2 | None | 10-05-18 | 01-09-19 2:22 PM | — | — | 7 | ✏️ 📄 |
| Client 3 | None | 10-05-18 | 01-09-19 2:22 PM | — | — | 7 | ✏️ 📄 |
| Client 4 | None | 12-21-18 | 01-09-19 3:13 PM | — | — | 7 | ✏️ 📄 |
| Client 5 | None | 10-05-18 | 01-09-19 3:13 PM | — | — | 9 | ✏️ 📄 |

1210

HOME>ASSIGN BY BILLER

THE BILLINGTOOL

DASHBOARD

WORKLISTS
Assign by Client
Assign by Biller

CLAIMS CENTER
Claims History
All Claims
Upload Claims
EClinical Upload

CONFIGURATION
Worklist Templates
Skip Reasons
Action Codes
Client Divisions
Manage Clients
Manage Biller Dashboard
Manage Users

ACCOUNT
Change Password
Log Out

Management > Provider Specialties

The Billing Tool Logo

Dashboard
Management
Forum
Technical Support
Submit Ticket
Actions
Add Specialty Fabian De La Pena Search  11/16/2017 1:00:33 PM Provider Specialties

| # | Name | Creation Date | Actions |
|---|---|---|---|
| 1 | Orthopedics | 9/18/2017 | ▶ |
| 2 | Neurology | 9/19/2017 | ▶ |
| 3 | Sports | 9/20/2017 | ▶ |
| 4 | Geriatrics | 9/21/2017 | ▶ |
| 5 | Women Health | 9/22/2017 | ▶ |
| 6 | Pediatrics | 9/23/2017 | ▶ |
| 7 | Clinical Electrophysiology | 9/24/2017 | ▶ |
| 8 | Cardiovascular and Pulmonary | 9/25/2017 | ▶ |

Worklist Templates

HOME>ALL WORKLIST TEMPLATES

Filters

Client: Select Some Options

[Apply Filters] [Reset Filters] [Set As Default] [Load Default]

Name: _____ [Create New Worklist Template]

Download As: .csv, .xls

18 WORKLIST TEMPLATES

| Name | Created | Manage Template |
|---|---|---|
| Agins SMG All Claims | 12-11-18 9:11 AM | ✎ 📋 |
| AMD>60 days | 10-29-18 4:28 PM | ✎ 📋 |
| AMD Claims by Balance | 10-23-18 3:02 PM | ✎ 📋 |
| AMD OBGYN Claims by Balance | 10-12-18 4:47 PM | ✎ 📋 |
| AMD OBGYN TOB | 12-17-18 9:30 AM | ✎ 📋 |

↙ 1510

Sidebar:
THE BILLINGTOOL

DASHBOARD

WORKLISTS
Assign by Client
Assign by Biller

CLAIMS CENTER
Claims History
All Claims
Upload Claims
EClinical
Upload

CONFIGURATION
Worklist
Templates
Skip
Reasons
Action Codes
Client
Divisions
Manage
Clients
Manage Biller
Dashboard
Manage Users ACCOUNT
Change
Password
Log Out

FIG. 15A

THE BILLINGTOOL

DASHBOARD

WORKLISTS
Assign by Client
Assign by Biller

CLAIMS CENTER
Claims History
All Claims
Upload Claims
EClinical Upload

CONFIGURATION
Worklist Templates
Skip Reasons
Action Codes
Client Divisions
Manage Clients
Manage Biller Dashboard
Manage Users

ACCOUNT
Change Password
Log Out

| | ○ Include ○ Exclude |
| --- | --- |
| | ○ Include ○ Exclude |
| | ○ Include ○ Exclude |
| | ○ Include ○ Exclude |
| | ○ Include ○ Exclude |

Multipliers

| Age from (days) | Age to (days) | Multiplier | Delete |
| --- | --- | --- | --- |
| | | | ☐ |
| | | | ☐ |
| | | | |
| | | | |
| | | | |

Other Options

Invert balance: ☐ Multiply all balances by -1 (billers will see lower balances first)

Biller sees all claims: ☑ If selected, the biller will see all claims for a particular patient regardless of filter choices (claims that do not match the filter will not count towards the manipulated balance)

Multiplier base value: ● Balance ○ Age  What initial value should be used for the manipulated balance Use dynamic age: ☑ If selected, the age of every claim will be updated daily. Otherwise, the age will be calculated according to the static age reference provided here: 01/31/2019

Default age (days): 14  If claim has no aging date, use this value

Followup default days: 14  Default followup selection for billers

Followup maximum days: 30  Maximum allowed followup for billers

Skip default days: 1  Default skip selection for billers

Skip maximum days: 14  Maximum allowed skip for billers

Save changes

Add Worklist

Priority Level Setting

High Priority: Denials ▸   ☐ New Denials  ☐ EMR Denials  ☐ Website Denials

Medium Priority: Age ▸   Min Age [45]   Max Age [70]

Low Priority: Follow Up ▸

Assign by Biller

Filters

Has Client Assignments: Select an Option | Client Division: Select Some Options | Worklist Templates: Select Some Options
Billers: Select Some Options | Client: Select Some Options

[Apply Filters] [Reset Filters] [Set As Default] [Load Default]

Download As: .csv, .xls

32 BILLERS

| Nickname | Last Login | Assignments | |
|---|---|---|---|
| spacheco | Jan. 30, 2019, 12:23 p.m. | 20 | Assignments + |
| rcannon | Jan. 13, 2019, 5:41 p.m. | 14 | Assignments + |
| rromero | Jan. 29, 2019, 2:46 p.m. | 13 | Assignments + |
| lmiller | Nov. 23, 2018, 4:13 a.m. | 13 | Assignments + |
| csmith | Jan. 30, 2019, 4:03 p.m. | 11 | Assignments + |
| dholloway | Jan. 30, 2019, 3:26 p.m. | 11 | Assignments + |

| Worklist template | Client | Target hours | Target claims | Hours worked (week) | Assigned claims | |
|---|---|---|---|---|---|---|
| Clinicient All Claims by Balance | Client 1 | 5 | None | 1.41 | 231 | Delete |
| Clinicient All Claims by Balance | Client 2 | 5 | None | 0.0 | 49 | Delete |
| Clinicient All Claims by Balance | Client 3 | 5 | None | 0.0 | 17 | Delete |
| Clinicient All Claims by Balance | Client 4 | 5 | None | 1.0 | 38 | Delete |
| PT All claims by Account Balance | Client 5 | 12 | 200 | 1.06 | 91 | Delete |

Worklist template: Select an Option
Client: Select an Option
Target hours:
Target client:

Sidebar:
- THE BILLINGTOOL
- DASHBOARD
- WORKLISTS
  - Assign by Client
  - Assign by Biller
- CLAIMS CENTER
  - Claims History
  - All Claims
  - Upload Claims
  - EClinical Upload
- CONFIGURATION
  - Worklist Templates
  - Skip Reasons
  - Action Codes
  - Client Divisions
  - Manage Clients
  - Manage Biller Dashboard
  - Manage Users
- ACCOUNT
  - Change Password
  - Log Out

HOME>ASSIGN BY BILLER

MEDICAL CLAIM DATABASE RELATIONSHIP PROCESSING

CROSS REFERENCE TO RELATED APPLICATION

This application claims benefit of U.S. Provisional Application Ser. No. 62/627,483 titled "Systems and Methods for Medical Claim Database Processing," filed Feb. 7, 2018, the entire disclosure of which is incorporated herein by reference.

FIELD OF THE DISCLOSURE

The present disclosure is generally related to database processing and more particularly is related to processing medical claims across databases for billing.

BACKGROUND OF THE DISCLOSURE

Medical billing in today's age can be complex for numerous reasons, one of which is the use of a multi-payer system where insurance companies are responsible for a portion of the costs for a patient and the patient is responsible for the remainder. When a medical claim or bill is issued, it is frequently coded with the proper medical billing codes and then it is sent to the patient's insurance company for review and processing. If there is an error in the medical coding, or if there is another issue with the bill, the insurance company may deny coverage. When this occurs, the medical office issuing the bill or the patient may need to contact the insurance company and determine why coverage was rejected and find out how to correct the bill. Due to the high volume of medical bills in insurance company processing departments, it can take an undesirable amount of time on the phone with a claims representative of the insurance company to identify the problem and correct it.

Because of the complexity and inefficiencies in this process, medical offices often rely on medical claims management companies to manage their billing and coordinate with the insurance companies for unpaid claims. The medical offices provide the medical claims management companies with their outstanding bills and the medical claims management companies call the insurance companies to identify the reason for the unpaid bill. Due to the high volume of claims, however, the insurance companies often limit the number of medical claims that can be discussed during one phone call. And, in many instances there is a wait time to speak to a representative at the insurance company, so it may only be possible for an employee at the medical claims management company to make 2-4 calls per hour. Thus, there is a practical ceiling of productivity for resolving unpaid medical claims.

Moreover, the inefficiency with this process is further complicated by the fact that medical claims are time sensitive. If the claim is not properly submitted to the insurance company within a certain period of time, commonly 90 days, the insurer can refuse to pay the claim. Similarly, medical claims are naturally for various monetary amounts, and the higher amounts are often more important to process than lower amounts. For example, given a claim for $30 and a claim for $3,000, both of which are nearing the end of the time period for processing, the medical office would certainly desire to process the larger claim first. However, it can be difficult to organize and manage the claims in such a way to handle the most important claims first, namely due to the lack of a management system for instructing the personnel at the medical claims management company which claims to process first.

Thus, for at least these reasons, a heretofore unaddressed need exists in the industry to address the aforementioned deficiencies and inadequacies.

SUMMARY OF THE DISCLOSURE

Embodiments of the present disclosure provide a system and method for electronic medical claims billing management. Briefly described, in architecture, one embodiment of the method, among others, can be implemented as follows. The method for electronic medical claims billing management includes collecting medical claim data from an EMR database of a medical provider. Insurance claim data is retrieved from a remote insurance database, wherein the insurance claim data corresponds to at least a portion of the medical claim data. A plurality of dashboards is provided on a computerized graphical user interface for viewing the collected medical claim data and the retrieved insurance claim data. The plurality of dashboards include at least a plurality of billing view dashboards, each providing a prioritization of a handling of a portion of the medical claim data to a medical claim analyst, wherein the medical claim analyst communicates with an insurance provider associated with the portion of the medical claim data according to a schedule determined by the prioritization, and at least one manager view dashboard providing workflow data corresponding to the plurality of billing view dashboards.

Embodiments of the present disclosure provide a system for medical claims billing management. Briefly described, in architecture, one embodiment of the system can be implemented as follows. The system includes at least one billing computer device, which has a processor and non-transitory computer-readable memory, a relational, subject-oriented electronic medical records (EMR) database of a medical provider containing multi-field medical claim data, and a remote insurance database containing multi-field insurance claim data corresponding to at least a portion of the medical claim data. The system also includes a server having a processor and non-transitory computer-readable memory. The server is accessible over at least one network system by the billing computer device, the EMR database, and the insurance database. A billing management application is hosted at least partially on the server. The billing management application collects multi-field medical claim data from the EMR database and retrieves multi-field insurance claim data from the insurance database. The billing management application also provides a plurality of dashboards on a computerized graphical user interface for viewing the collected medical claim data and the retrieved insurance claim data, wherein each of the plurality of dashboards provides a prioritization of a handling of a portion of the medical claims data to a medical claim analyst, wherein the medical claim analyst communicates with an insurance provider associated with the portion of the medical claims data according to a schedule deter mined by the prioritization. Additionally, the billing management application provides at least one manager view dashboard providing workflow data corresponding to the plurality of billing view dashboards.

Embodiments of the present disclosure provide a system and method for processing relationships in a medical claims database. Briefly described, in architecture, one embodiment of the method, among others, can be implemented as follows. A method for processing relationships in a medical claims database using a computerized system having a processor and a non-transitory memory includes storing multi-field medical claim data and multi-field insurance claim data in a relational electronic database. The insurance claim data corresponds to at least a portion of the medical claim data. A worklist template is defined using at least one filter and at least one multiplier. The at least one filter excludes at least a portion of the medical claim data, and the at least one multiplier defines a weighted value applicable to at least one field of the multi-field medical claim data. The processor converts the medical claim data into standardized values by applying the at least one multiplier to at least one field of the multi-field medical claim data. A biller worklist is assigned based on a hierarchy of the standardized values.

Other systems, methods, features, and advantages of the present disclosure will be or become apparent to one with skill in the art upon examination of the following drawings and detailed description. It is intended that all such additional systems, methods, features, and advantages be included within this description, be within the scope of the present disclosure, and be protected by the accompanying claims.

BRIEF DESCRIPTION OF THE DRAWINGS

Many aspects of the disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views.

FIG. 2 is a flow chart showing a method for medical claims billing management using a computerized system, in accordance with a second exemplary embodiment of the present disclosure.

FIG. 5 shows a note menu of the billing application, in accordance with the first exemplary embodiment of the present disclosure.

FIG. 6 shows a skip menu of the billing application, in accordance with the first exemplary embodiment of the present disclosure.

FIG. 7 shows a worked claims dashboard of the billing application, in accordance with the first exemplary embodiment of the present disclosure.

FIG. 11 shows a teams page of the billing application, in accordance with the first exemplary embodiment of the present disclosure.

FIG. 12 shows a clients page of the billing application, in accordance with the first exemplary embodiment of the present disclosure.

FIG. 13 shows an EMRs page of the billing application, in accordance with the first exemplary embodiment of the present disclosure.

FIG. 14 shows a provider specialties page of the billing application, in accordance with the first exemplary embodiment of the present disclosure.

FIG. 15A shows a worklists templates page of the billing application, in accordance with the first exemplary embodiment of the present disclosure.

FIGS. 15B-15D show worklist editing menus of the worklists page, in accordance with the first exemplary embodiment of the present disclosure.

FIG. 16 shows a billers' clients page of the billing application, in accordance with the first exemplary embodiment of the present disclosure.

FIG. 17 shows a billers page of the billing application, in accordance with the first exemplary embodiment of the present disclosure.

FIG. 19 shows a filter templates page of the billing application, in accordance with the first exemplary embodiment of the present disclosure.

FIG. 20 shows a priority templates page of the billing application, in accordance with the first exemplary embodiment of the present disclosure.

FIG. 21 shows a technical support page of the billing application, in accordance with the first exemplary embodiment of the present disclosure.

DETAILED DESCRIPTION

In the following description, reference is made to the accompanying drawings, which form a part hereof, and in which is shown, by way of illustration, various embodiments of the present disclosure. It is understood that other embodiments may be utilized and changes may be made without departing from the scope of the present disclosure.

Many embodiments of the disclosure may take the form of computer-executable instructions, including algorithms executed by a programmable computer. However, the disclosure can be practiced with other computer system configurations as well. Certain aspects of the disclosure can be embodied in a special-purpose computer or data processor that is specifically programmed, configured or constructed to perform one or more of the computer-executable algorithms described below. Accordingly, the term "computer" as generally used herein refers to any data processor and includes Internet appliances, hand-held devices (including palm-top computers, wearable computers, cellular or mobile phones, multi-processor systems, processor-based or programmable consumer electronics, network computers, minicomputers) and the like.

The disclosure also can be practiced in distributed computing environments, where tasks or modules are performed by remote processing devices that are linked through a communications network. Moreover, the disclosure can be practiced in Internet-based or cloud computing environments, where shared resources, software and information may be provided to computers and other devices on demand. In a distributed computing environment, program modules or subroutines may be located in both local and remote memory storage devices. Aspects of the disclosure described below may be stored or distributed on computer-readable media, including magnetic and optically readable and removable computer disks, fixed magnetic disks, floppy disk drive, optical disk drive, magneto-optical disk drive, magnetic tape, hard-disk drive (HDD), solid state drive (SSD), compact flash or non-volatile memory, as well as distributed electronically over networks including the cloud. Data structures and transmissions of data particular to aspects of the disclosure are also encompassed within the scope of the disclosure.

Figure 1A:
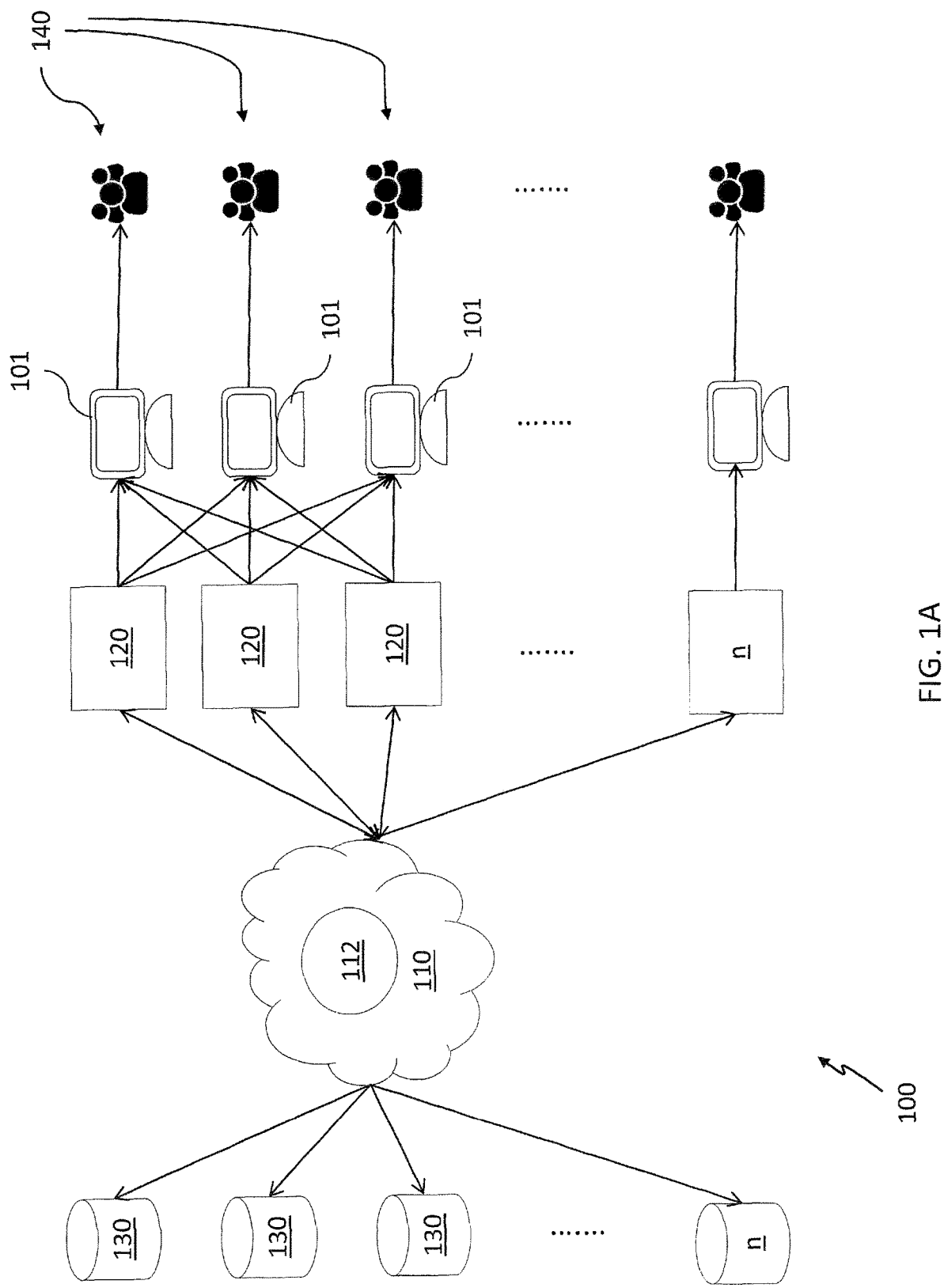
FIG. 1A is a box diagram of a system for medical claims billing management, in accordance with a first exemplary embodiment of the present disclosure.

FIG. 1A is a box diagram of a system 100 for medical claims billing management, in accordance with a first exemplary embodiment of the present disclosure. The system 100 includes at least one billing computer device 101, which has a processor and non-transitory computer-readable memory, a relational, subject-oriented electronic medical records (EMR) database 120 of a medical provider containing multi-field medical claim data, and a remote insurance database 130 containing multi-field insurance claim data corresponding to at least a portion of the medical claim data. The system 100 also includes a server 110 having a processor and non-transitory computer-readable memory. The server 110 is accessible over at least one network system by the billing computer device 101, the EMR database 120, and the insurance database 130. A billing management application 112 is hosted at least partially on the server 110. The billing management application 112 collects multi-field medical claim data from the EMR database 120 and retrieves multi-field insurance claim data from the insurance database 130. The billing management application 112 also provides a plurality of dashboards on a computerized graphical user interface for viewing the collected medical claim data and the retrieved insurance claim data, wherein each of the plurality of dashboards provides a prioritization of a handling of a portion of the medical claims data to a medical claim analyst, wherein the medical claim analyst communicates with an insurance provider associated with the portion of the medical claims data according to a schedule determined by the prioritization. Additionally, the billing management application 112 provides at least one manager view dashboard providing workflow data corresponding to the plurality of billing view dashboards. The billing view and management dashboards are discussed in greater detail in FIGS. 3-21.

The billing computer device 101 may be any electronic computer device capable of accessing the billing management application 112 or the EMR database 120, including personal computers, laptop computers, tablets, smartphones, and the like. By way of example, the billing computer device 101 is shown in FIG. 1A as a desktop computer. As also shown in FIG. 1A, the system 100 may include multiple billing computer devices 101 used by users 140 of the billing management application 112. Users 140 may be billers, medical office clients, managers, or administrators.

Multi-field medical claim data may be electronic data encompassing to two or more fields relevant to medical claims. For example, relevant data for a single medical claim may include a patient identifier, such as a name, plan number, or social security number, a claim date, a claim amount or balance, CPT codes, claim status information, medical provider information, insurance payer information, and the like. Each medical claim entry in the EMR database 120 may include a plurality of data fields, thus the medical claim data may be multi-field data. In this disclosure, a medical claim entry containing multiple data fields may be called "medical claim information" or "health-related information," and any reference therein to "information" may be considered to include the multi-field medical claim data as discussed above. Likewise, multi-field insurance claim data may be electronic data encompassing two or more fields relevant to insurance claims. At least a portion of the fields may correspond to the medical claim data fields. In this disclosure, an insurance claim entry containing multiple data fields may be considered to be "insurance claim information." In this capacity, any reference to information may be understood to pertain to electronic data.

The EMR database 120 contains an electronic record of health-related information on an individual within a health care organization. The EMR database 120 may be a relational, subject-oriented database or data warehouse system used for providing electronically accessible medical records, and may include components commonly used in databases, such as a power source, processor, computer-readable memory, a network connection, and the like. As a subject-oriented database, the EMR database 120 may be organized and structured around a subject, namely a medical claim or an individual, such as a patient. This database structure may allow multi-field data from one or more medical incidents or claims to be organized in relation to one another. As a relational database, the data stored within the EMR database 120 may be organized by relations according to categories of information. In one example, the EMR database 120 may be a distributed series of databases 120 containing electronic medical claim information. The distributed database may be a homogenous distributed database, having the same management systems across each node in the database. In another example, the billing management application 112 may connect to multiple different EMR databases 120 to provide comprehensive medical claims billing to a variety of clients. The EMR database 120 may also provide a software interface for users 140 to access medical claim information using a billing computer device 101. The billing management application 112 may work together with the EMR database 120 to accomplish the medical claims billing described herein.

Medical claim information may be stored on the EMR database 120. Medical claim information may include a patient's identifying information, medical history, and a record of medical services for which a medical office has submitted medical claims. The record may particularly include the monetary balance of claims, the date when the claim was made, and the insurance provider, or payer, the claim was made to. For example, the monetary balance may include an amount billed by a medical service provider, a negotiated amount agreed upon between a service provider and an insurance provider, or a remaining balance after a partial payment. The claim date may include the date when medical services were provided, the date when the claim was filed, or the date when the claim was updated. The insurance provider may include the name or unique identifier of the insurance provider. Medical claim information may also include a unique identifier for the claim, a patient identifier, a client identifier, a claim status, CPT codes, and other metadata helpful in processing a medical claim. For example, a unique identifier for the claim may be a name or number used as an internal reference in order to identify claims within the system. A patient identifier may be a name, patient number, or other identifying information regarding the patient who received the medical services. A client identifier may be a name, client number, or other identifying information used to identify the medical service provider seeking payment and processing of the medical claim. A claim status may indicate whether a medical claim is being processed, has been skipped, is reaching a particular age, or has a priority based on its monetary value, client, or other factors. CPT codes may refer to current procedural terminology codes used in medical billing to identify medical procedures in a standardized format. Other metadata may include the date when the claim was first processed in the system, the frequency with which the claim has been accessed, and the like.

The insurance database 130 may be any system commonly used for providing electronically accessible medical records, and may include components commonly used in databases, such as a power source, processor, computer-readable memory, a network connection, and the like. The insurance database 130 contains an electronic record of insurance claim information corresponding to at least a portion of the medical claim information. As an example, if an insurance company received a medical claim bill for a service performed by a medical office, the insurance company would keep a record of that medical claim bill in an insurance database 130. The insurance database 130 may also include information about the processing or payment status of the medical claim by the insurance company. For instance, if a medical claim has been completely processed and paid out, the insurance database 130 would include information reflecting that. If a medical claim is awaiting processing, the insurance database 130 would include information reflecting that. If a medical claim cannot be processed further because of an error or a dispute, the insurance database 130 would reflect that. Each insurance company may have one or more insurance databases 130 to store electronic records of insurance claim information.

The server 110 may be any system commonly used for hosting software programs, processing data, and communicating with other devices. The server 110 may include a processor and non-transitory computer-readable memory, along with other components commonly used in server devices. In particular, the server 110 may include a central database that can be used to store information retrieved from EMR databases 120 and insurance databases 130. The server is accessible by the billing computer device 101, the EMR database 120, and the insurance database 130 over at least one network system. The network system may be any interconnected network of the above devices, including over the Internet, Local Area Network (LAN), wireless connections such as WiFi, cellular networks, Bluetooth® and the like, and intranets.

A billing management application 112 (hereinafter "billing application 112") is hosted at least partially on the server. The billing application 112 may access medical claim information on the EMR database 120 and insurance claim information on the insurance database 130, and copy and consolidate the medical claim information and insurance claim information into a single report or other document. The billing application 112 may access the EMR database 120 and insurance database 130 using the at least one network system and through an appropriate platform. In software, these functions may be performed through multiple software modules.

In one example, automated billing collector modules may be responsible for collecting medical claim information from one or more EMR databases 120 and feeding the information to the server 110. Each EMR database 120 may require a different collector module to interface with the database 120. In another example, the billing application 112 may use an Open Database Connectivity (ODBC) interface or other Application Programming Interface (API) to directly locate and copy the medical claim data in a number of different insurance databases 130. ODBC and API platforms may provide more robust access to a variety of databases. For example, the billing application 112 using an ODBC interface may use an ODBC driver to translate between the billing application 112 and the database management system (DBMS). The ODBC driver may automatically query the EMR database 120 for medical claim information using a standard query language. Other APIs may be directed to particular DBMS or database control protocols in order to query the EMR database 120 and collect data. In one example, the billing application 112 may use a combination of platforms.

In another example, manual billing collector modules may be responsible for collecting medical claim information from reports that were uploaded manually to the EMR database 120. Each EMR database 120 may require a different manual billing collector module to interface with the database 120.

In one example, the billing application 112 may use web scraping to access an EMR database 120 either locally or through a web portal, automatically navigating the database 120 and copying or exporting medical claim information into the database 120. Web scraping may include fetching a web page corresponding to a claim in the EMR database 112 and extracting data from data fields on the page. The data may be parsed to extract relevant claim information or reformatted to a standardized format for use within the system.

In another example, billing observer modules may be responsible for retrieving insurance claim information from one or more insurance databases 130 and feeding the information to the server 110. Each insurance database 130 may require a different billing observer module to interface with the database 130. Similar to the automated billing collector modules, the billing observer modules may access the insurance databases 130 through one or more methods such as web scraping, API, or ODBC interfaces. Relevant information may be copied to the server 110 for later use.

In another example, billing reporter modules may be responsible for reporting insurance claim information from the insurance database 130 to the EMR database 120. Each EMR database 120 may require a different billing reporter module to interface with the database 120. The billing reporter modules may report insurance claim information using API, ODBC, or any other database access and writing methods commonly used.

In another example, a central controller module may coordinate usage and implementation of all of the software modules in the billing application 112. This may include triggering the billing observer modules to obtain new or updated insurance claim information from the insurance databases 130 and triggering the billing reporter modules to report insurance claim information to the appropriate EMR database 120. This may also include triggering the automatic and manual collector modules to periodically query an appropriate EMR database 120 for medical claim information. Additionally, the central controller module may control a graphical user interface (GUI) to provide a platform for a user 140.

The GUI provides an interface for one or more users 140 to perform medical claim billing management using the system 100. In one example, client users 140 may use the GUI to see the status of pending claims. In another example, biller users 140 may use the GUI to sort and process medical claims according to a prioritization schedule determined by the billing application 112. In another example, administrative users 140 may use the GUI to monitor the work of billers processing claims in the system 100.

The billing application 112 may be accessed a number of different ways, including through a web portal, as a software program stored on the billing computer device 101, as a downloadable application, and the like. By way of example in FIG. 1A, the billing application 112 is accessed through a web portal using the Internet.

Figure 1B:
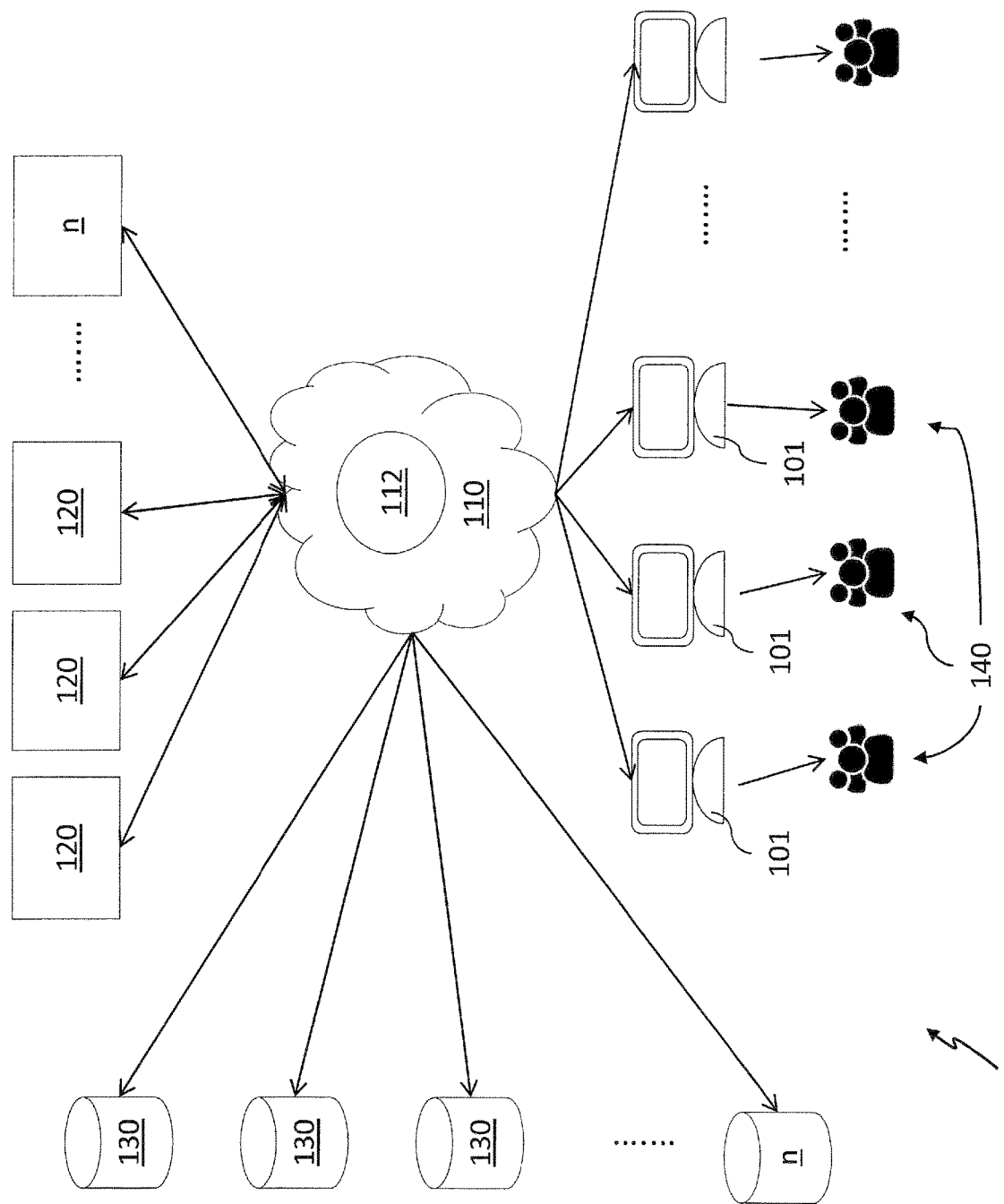
FIG. 1B is a box diagram of a system for medical claims billing management, in accordance with a second exemplary embodiment of the present disclosure.

FIG. 1B is a box diagram of a system 100 for medical claims billing management, in accordance with a second exemplary embodiment of the present disclosure. In FIG. 1B, the billing computer devices 101 are not directly connected to the EMR databases 120, but instead are directly connected to the server 110 and the billing application 112. Users 140 may access the billing application 112 through a web portal, software program, or application on a billing computer device 101, which obtains all of the retrieved and collected medical claim information and insurance claim information stored on the server 110.

Prioritization Schedule

Once the billing application 112 has collected and retrieved the medical claim information and the corresponding insurance claim information, it may develop a prioritization schedule for processing any outstanding claims. The prioritization schedule may allow a client to process outstanding claims in an optimal manner, maximizing the number of claims processed, the dollar amount processed, the number of patients processed, or some combination thereof. In operation, the billing application 112 may prioritize claims according to various algorithms or schedules. For example, the system may have a standard prioritization algorithm which is used. However, the manager view may allow the manager to customize the prioritization by applying different weights to the various measures. For example, the standard algorithm to prioritize claims may be based on the balance outstanding combined with a multiplier based on the age of the claim. However, the manager may adjust the focus on specific aspects of the claims. For example, the manager may want to put even more focus on older claims, as opposed to, for example, claims with a high monetary value. In this instance they could add more weight to the age of the claim so that older claims would appear higher in the prioritized list even if their dollar amount was less than a younger claim.

Operating Example

The following operating examples may illustrate how the billing application 112 is used in implementation.

A client user 140 may use the system 100 to check the status of several claims pending for the client's medical office. The client may log into the billing application 112 using a billing computer device 101, entering identifying information such as the client's name and password, the medical office name, and information regarding the claims the client wants to check. The billing application 112 may authenticate the client and process the claim information using the automated or manual billing collector modules. The billing collector modules may verify that the claims are located in an EMR database 120, collecting any necessary claim information in the process and storing it on the server 110. A billing observer module may use relevant claim information to query an insurance database 130 for insurance claim information corresponding to the medical claim information, retrieving any relevant information, including status information, and storing it on the server 110. A billing reporter module may process the medical claim information and the insurance information together to provide a status update for the client user 140, reporting the status update to the EMR database 120 or via the GUI to the billing computer device 101. The client user 140 may view the status update, annotate particular claims, or use the billing application 112 to pursue certain claims further.

In another example, a biller user 140 may use the system 100 to receive a prioritization schedule for medical claims. The biller may log into the billing application 112 using a billing computer device 101, entering identifying information such as the biller's name and password, a client's name, and information regarding the claims the biller wants to work on. The billing application 112 may authenticate the biller and process the claim information using the automated or manual billing collector modules. The billing collector modules may verify that the claims are located in an EMR database 120, collecting any necessary claim information in the process and storing it on the server 110. A billing observer module may use relevant claim information to query an insurance database 130 for insurance claim information corresponding to the medical claim information, retrieving any relevant information and storing it on the server 110. A billing reporter module may process the medical claim information and the insurance information together, and the billing application 112 may use this information to generate a prioritized worklist for the biller. The biller may view and interact with the worklist using the GUI of the billing application 112. As the biller processes claims, they may be cleared or annotated in the billing application 112.

In another example, a manager or administrator user 140 may use the system 100 to monitor the work progress of one or more billers using the billing application. The manager may log into the billing application 112 using a billing computer device 101, entering identifying information such as the manager's name and password, a client's name, or information regarding the biller the manager wishes to monitor. The billing application 112 may authenticate the manager and direct them to a manager dashboard via the GUI. The manager may navigate through pages on the manager dashboard to monitor work by biller, client, teams of billers, and the like. The manager may create or adjust worklists, assigning tasks to one or more billers. The monitor may additionally view analytic reports regarding productivity and adjust worklists according to those reports.

The GUI of the billing application 112 may be better understood by way of the plurality of dashboards it provides. The plurality of dashboards is discussed in greater detail in FIGS. 3-21.

FIG. 2 is a flow chart 200 showing a method for medical claims billing management using a computerized system having a processor and non-transitory memory. It should be noted that any process descriptions or blocks in flow charts should be understood as representing modules, segments, or steps that include one or more instructions for implementing specific logical functions in the process, and alternate implementations are included within the scope of the present disclosure in which functions may be executed out of order from that shown or discussed, including substantially concurrently or in reverse order, depending on the functionality involved, as would be understood by those reasonably skilled in the art of the present disclosure.

In step 210, medical claim information is electronically collected from an electronic medical records (EMR) database of a medical provider. In step 220, insurance claim information is electronically retrieved from an insurance database, wherein the insurance claim information corresponds to at least a portion of the medical claim information.

In step 230, a plurality of dashboards is provided on a computerized graphical user interface for viewing the collected medical claim information and the retrieved insurance claim information. The plurality of dashboards comprises at least a plurality of billing view dashboards, each providing a prioritization of a handling of a portion of the medical claims information to a medical claim analyst. The medical claim analyst communicates with an insurance provider associated with the portion of the medical claims information according to a schedule determined by the prioritization. The plurality of dashboards also comprises at least one manager view dashboard providing workflow information corresponding to the plurality of billing view dashboards.

FIGS. 3-21 show graphical user interface views of the plurality of billing view dashboards and the at least one manager view dashboard. It should be understood that these figures represent exemplary implementations of the software dashboards, and that other implementations are included within the scope of this disclosure.

Figure 3:
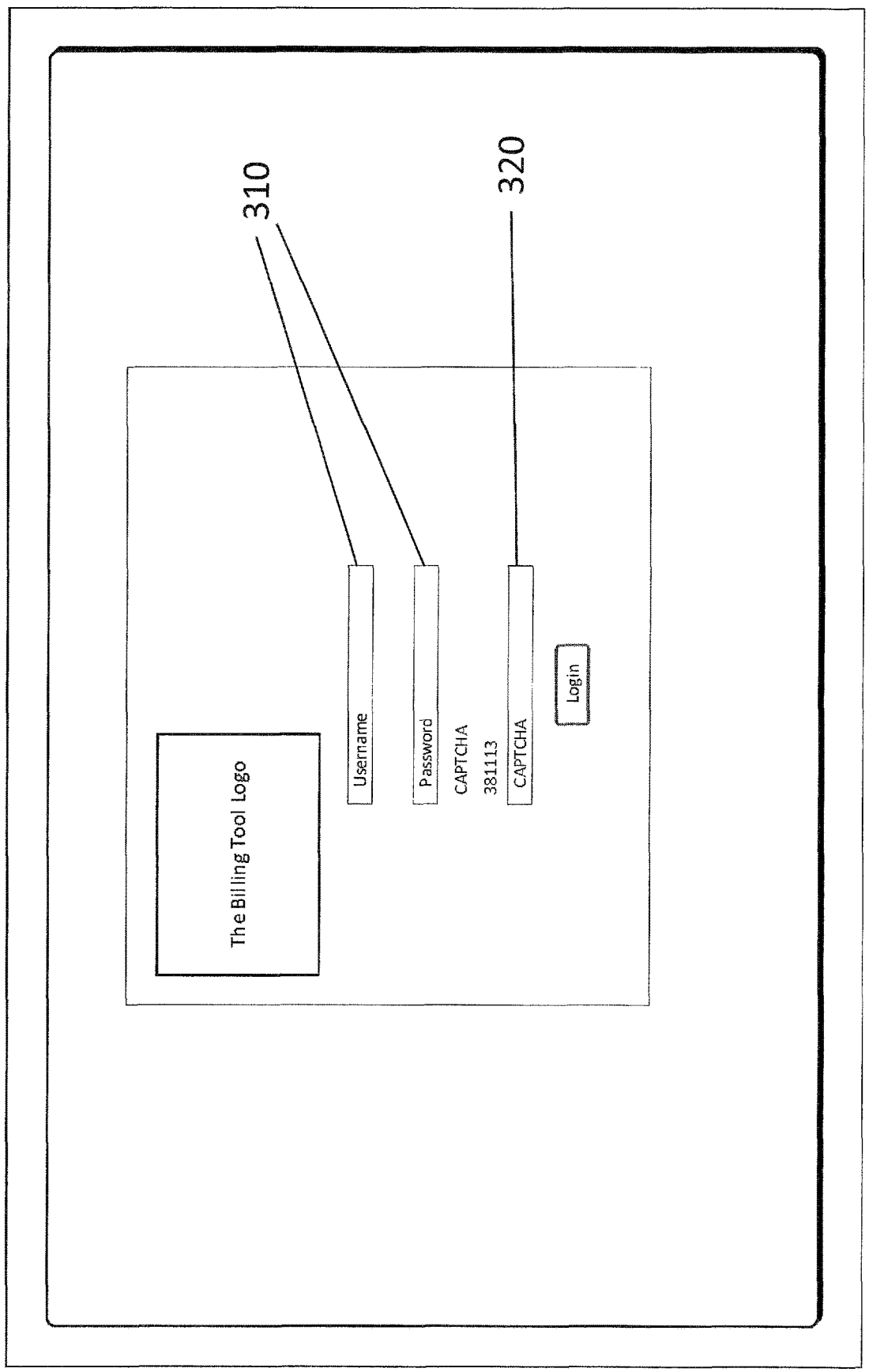
FIG. 3 shows a log-in page for a user of the billing application, in accordance with the first exemplary embodiment of the present disclosure.

FIG. 3 shows a log-in page 300 for a user of the billing application 112. The log-in page 300 may contain form fields 310, 320 that can be filled in by a user. In one example, the form fields 310 may prompt the user to enter identifying and authenticating information, such as a username, password, company ID, access codes, and the like. In another example, the form fields 320 may prompt the user to prove they are human, such as by entering a CAPTCHA code, checking an "I'm not a robot" box, identifying visual information in images, and the like. In another example, the log-in page 300 may prompt the user to select an aspect of the billing application 112, such as billing view or manager view, they'd like to log in to.

Figure 4:
FIG. 4 shows a worklist page of the billing application, in accordance with the first exemplary embodiment of the present disclosure.

FIG. 4 shows a worklist page 410 of a worklist dashboard 400. A user may access the worklist dashboard 400 by clicking on a worklist button. The worklist dashboard 400 may provide an interface for a medical claim analyst to pursue claims according to a claim prioritization schedule. The worklist may be organized according to medical service provider (also known as the client), patient, insurer, initial claim submission date, claim balance, or any combination thereof. By way of example in FIG. 4, the worklist is organized first by the client, which is shown in box 420. The billing application 112 may create a worklist for each client, which can be displayed on the worklist page 410. Box 430 shows a portion of the worklist page 410 that displays information about a particular patient with outstanding claims. Box 430 may display identifying information about the patient, such as name, date of birth, and the client with which the patient is linked, among others. Box 440 shows a portion of the worklist page 410 that displays insurance claim information associated with medical claim information. By way of example, such information may include the insurance payer name, the EMR claim number, the claim submission date, the claim balance, the status of the claim, a proposed follow-up date for the claim, the last date on which the claim was submitted, and other details regarding the claim. Multiple claims may be shown in a list within box 440. When multiple claims are shown, box 440 may also show totals or subtotals for the claim balance amounts, the number of claims, and the claims coming due in the near future. Box 440 may also include an "action" column for annotating a particular claim or skipping the claim within the worklist.

Figure 5:
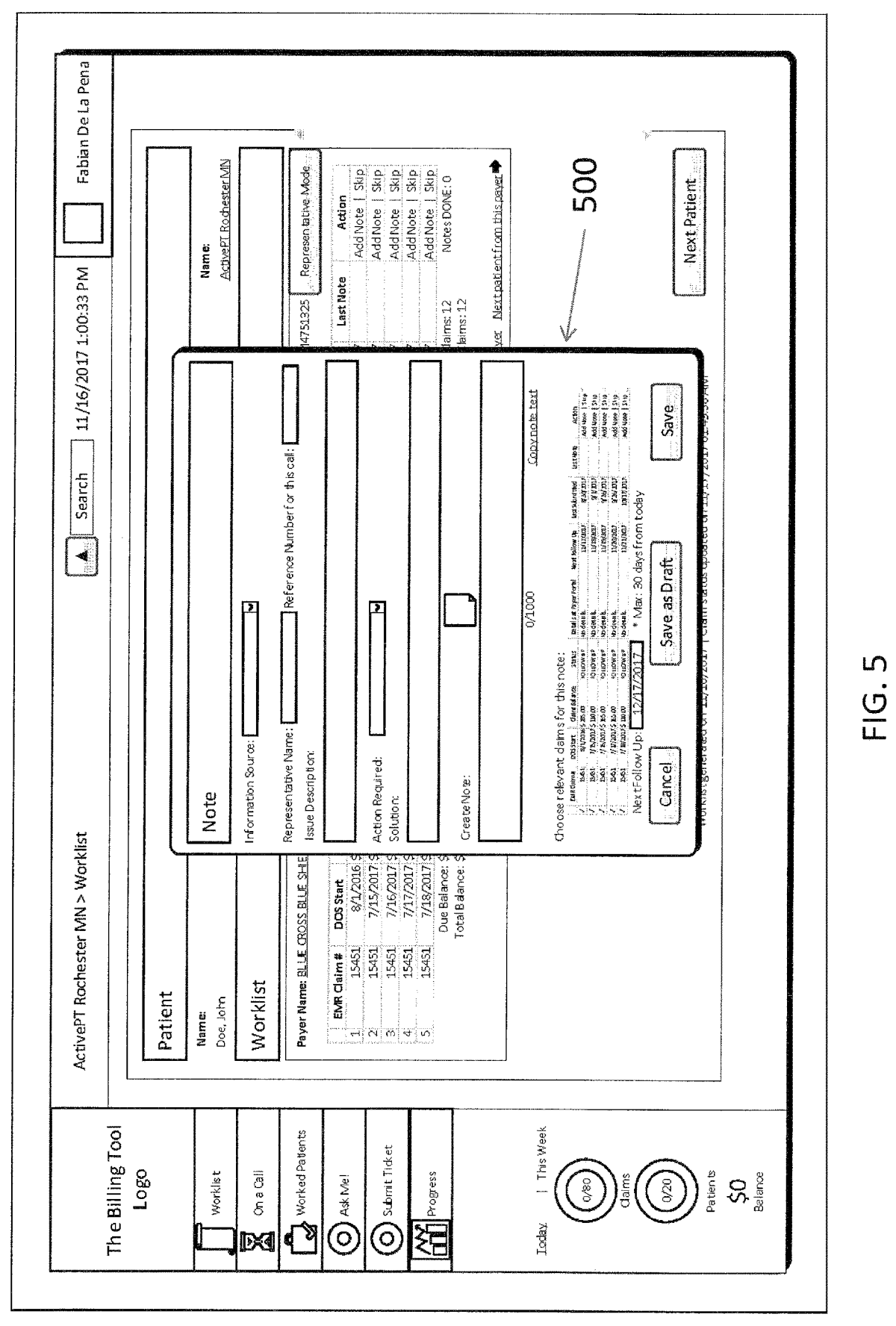

FIG. 5 shows a note menu 500 that may be accessed when a user clicks the "Add Note" button under the "action" column in FIG. 4. The note menu 500 may allow a user to enter notes relevant to one or more claims. Such notes may correspond to issues raised during a phone call with the payer, actions to be taken to resolve the issues, and other information as desired. Notes may be linked to one or more claims and saved into the system 100.

Figure 6:
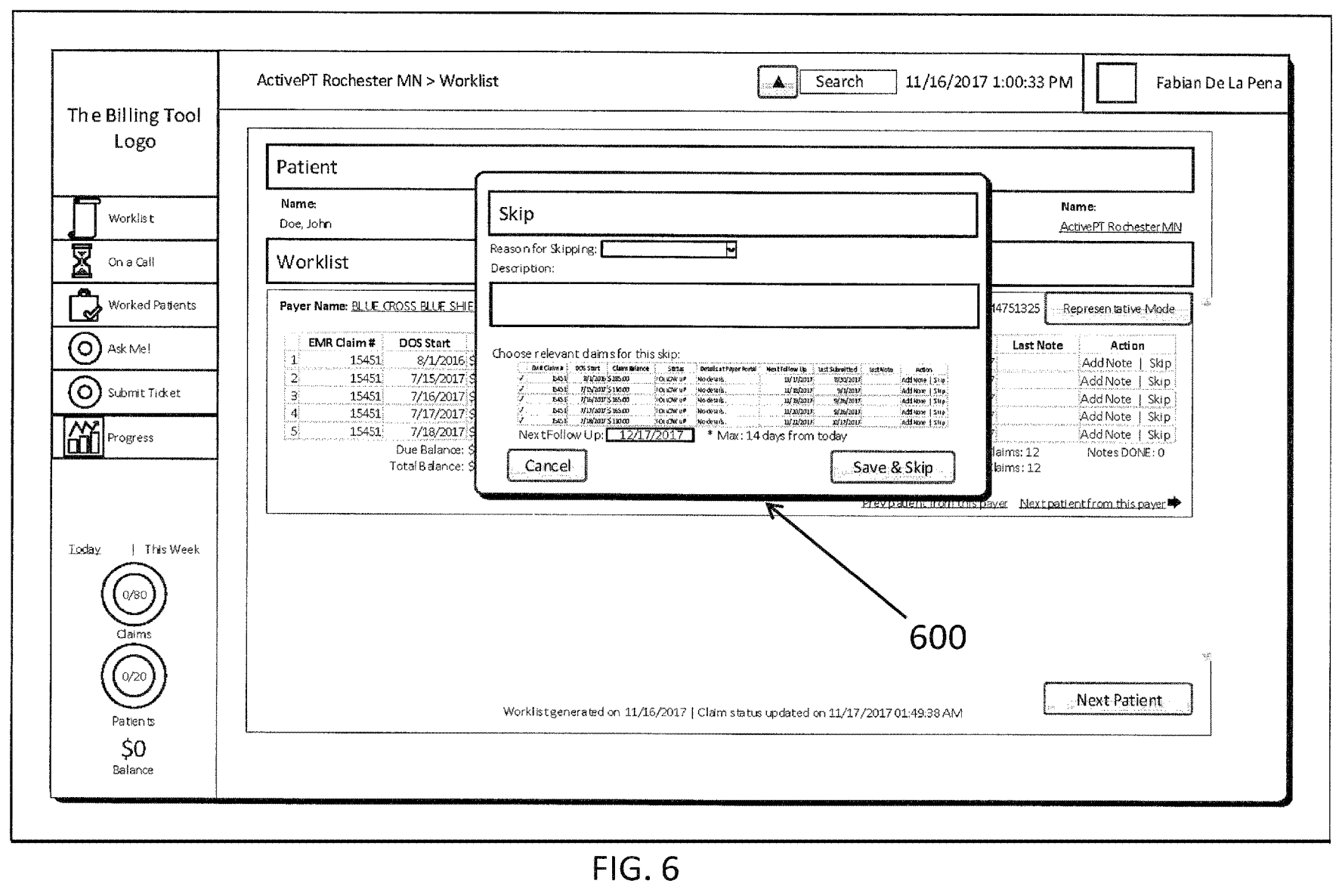

FIG. 6. shows a skip menu 600 that may be accessed when a user clicks the "Skip" button under the "action" column in FIG. 4. The skip menu 600 may allow a user to skip work on one or more claims. The user may be able to enter a reason for skipping the claims along with a brief description of the reason. Skipping requests may be linked to one or more claims and saved into the system.

FIG. 7 shows a worked claims dashboard 710 that may be accessed by clicking on the Claims History button 700. The worked claims dashboard 710 may include information about each claim currently in the billing application 112. Such information may include a patient's name, the provider client associated with the patient, the balance processed (also known as worked balance), the number of claims worked, the number of remaining claims, the patient status, the last update of the patient's status, and the like. Multiple claims may be shown in a list, and the list may be organized according to any of the categories of information displayed. The worked claims dashboard 710 may allow a user to quickly assess the status of one or more patients in order to optimally determine which claims to process.

Figure 8:
FIG. 8 shows a progress dashboard of the billing application, in accordance with the first exemplary embodiment of the present disclosure.

FIG. 8 shows a progress dashboard 810 that may be accessed by clicking on the Progress button 800. The progress dashboard 810 may include information indicating the amount of work progress one or more users has made on processing claims for a list of clients. Such information may include the client's name, a target number of hours of work, the number of hours completed so far, the number of remaining hours, and the like. The target number of hours may be set by the billing application, a manager, or another user. Progress information may be managed by clicking on a "Manage Login" button associated with the client.

Figure 9:
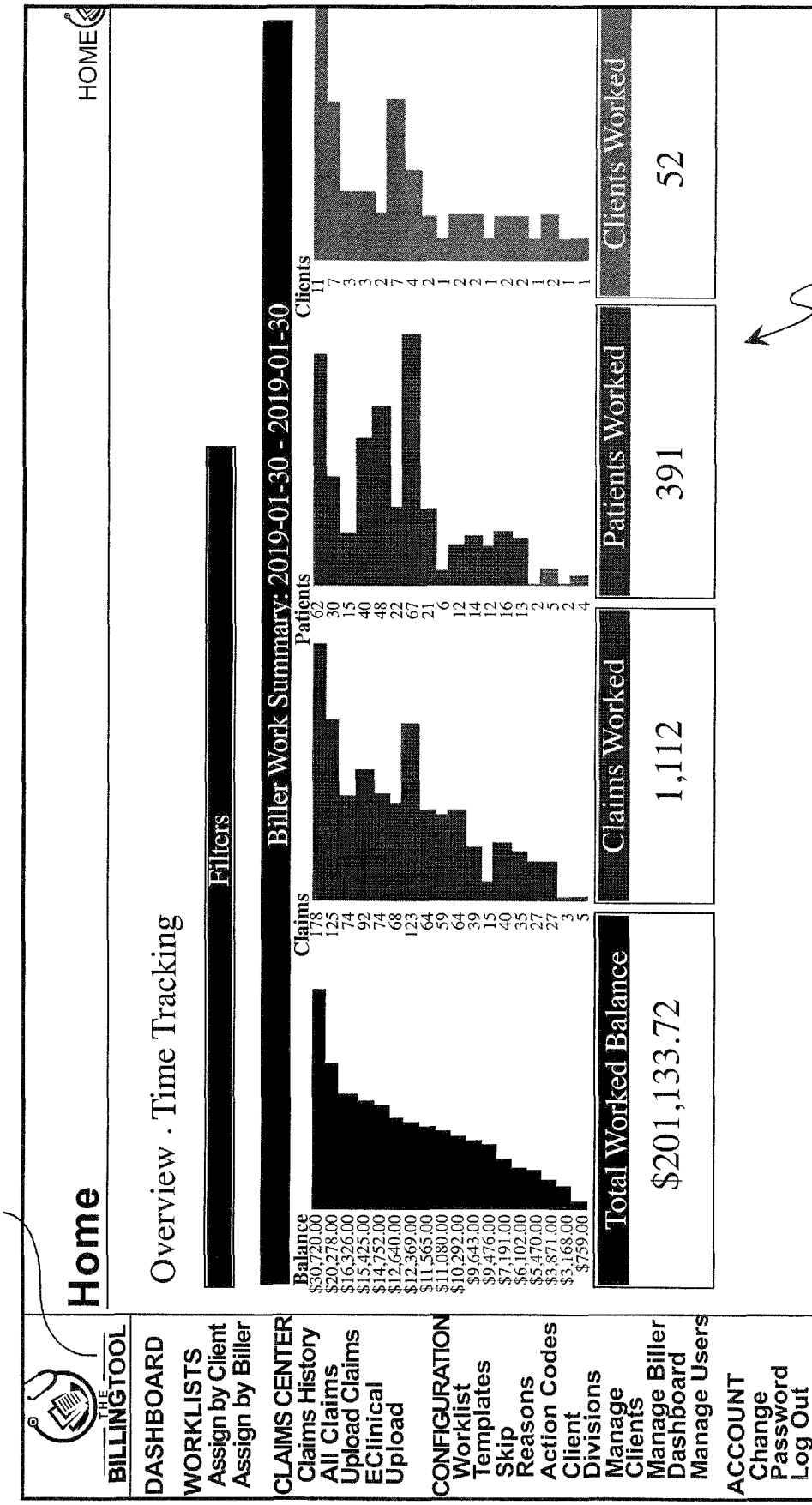
FIG. 9 shows a management dashboard of the billing application, in accordance with the first exemplary embodiment of the present disclosure.

FIG. 9 shows a management dashboard 910 that may be accessed by clicking on the Dashboard button 900. The management dashboard 910 may provide information pertaining to the work done by one or more billers processing claims using the billing application 112. For example, the management dashboard 910 may provide information about the claim balances processed by each biller, including individual and total balances. As another example, the management dashboard 910 may provide information about the number of claims completed by each biller, including individual and total numbers. The management dashboard 910 may also provide information about the total number of patients processed, the number of clinics served, progress made toward a target goal, and the like.

Figure 10:
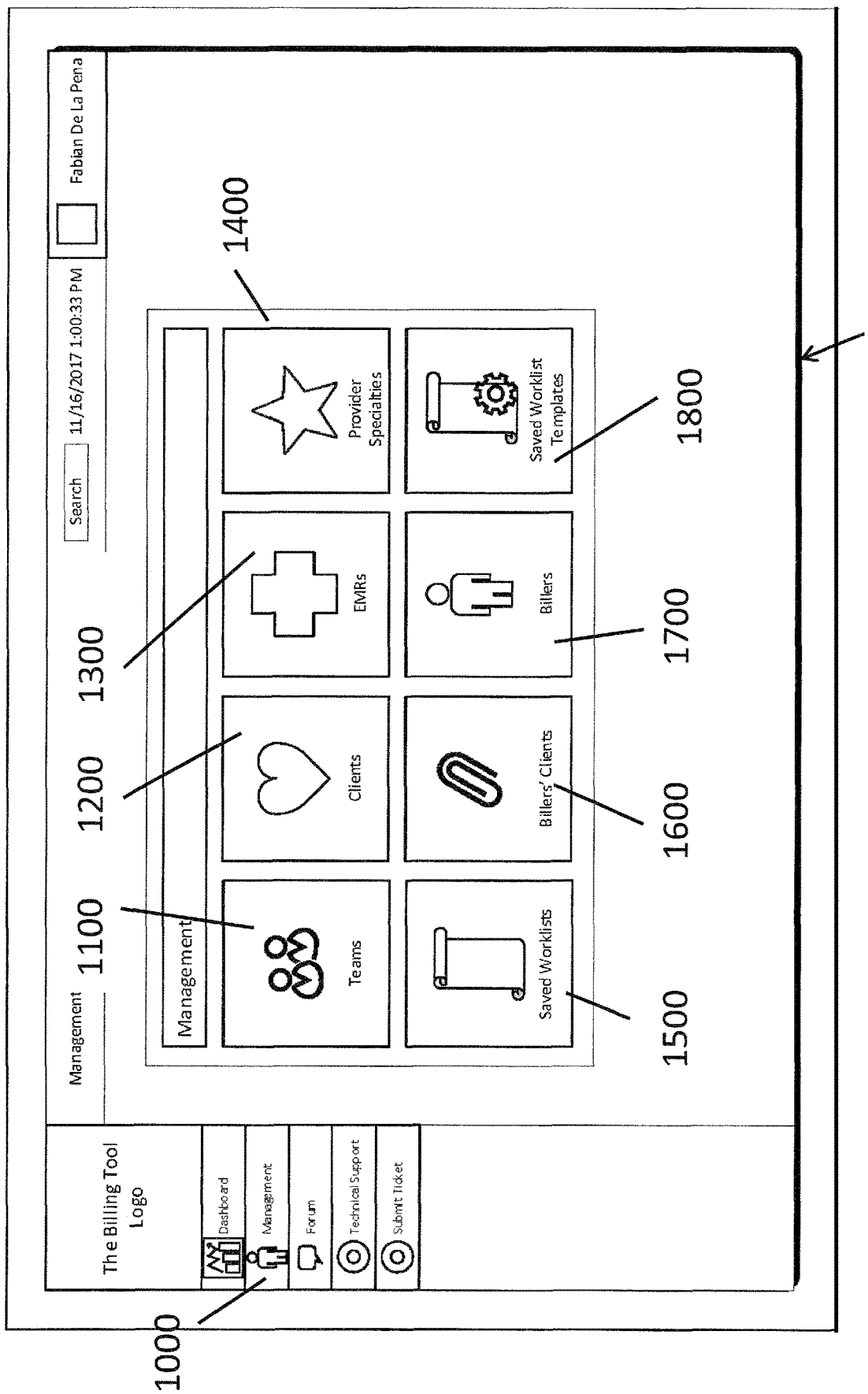
FIG. 10 shows a management navigation page of the billing application, in accordance with the first exemplary embodiment of the present disclosure.

FIG. 10 shows a management navigation page 1010 that may be accessed by clicking on the Management button 1000. The management navigation page 1010 may provide a managing user with navigation options to additional management pages within the management dashboard 910. By way of example, FIG. 10 shows a Teams button 1100, a Clients button 1200, an EMRs button 1300, a Provider Specialties button 1400, a Saved Worklists button 1500, a Billers' Clients button 1600, Billers button 1700, and a Saved Worklist Templates button 1800. The buttons 1100-1800 may contain graphic elements, text elements, or a combination of the two. The buttons 1100-1800 lead to the additional management pages discussed in FIGS. 11-21, below.

FIG. 11 shows the teams page 1110 that may be accessed by clicking on the Teams button 1100 shown in FIG. 10. The teams page 1110 may provide information about the billing teams working within the billing application 112. For example, the teams page 1110 may include a list of team numbers, team names, a manager in charge of each team, the date when the team was created, and the like. The teams page 1110 may include an "action" column to allow a managing user to annotate an entry, edit team information, or create a new team entry.

FIG. 12 shows the clients page 1210 that may be accessed by clicking on the Manage Clients button 1200 shown in FIG. 10. The clients page 1210 may provide information about the clients who have worklists within the billing application 112. For example, the clients page 1210 may include a list of clients organized by client number, name, starting date, the billing team assigned to the client, the names of the billing team members, and the like. The clients page 1210 may include an "action" column to allow a managing user to annotate an entry, edit the information, or create a new entry. The clients page 1210 may also include a "filters" column to allow a user to apply filters, reset filters, create a default filter setting, load a default filter, or create additions to the page.

Figure 13:
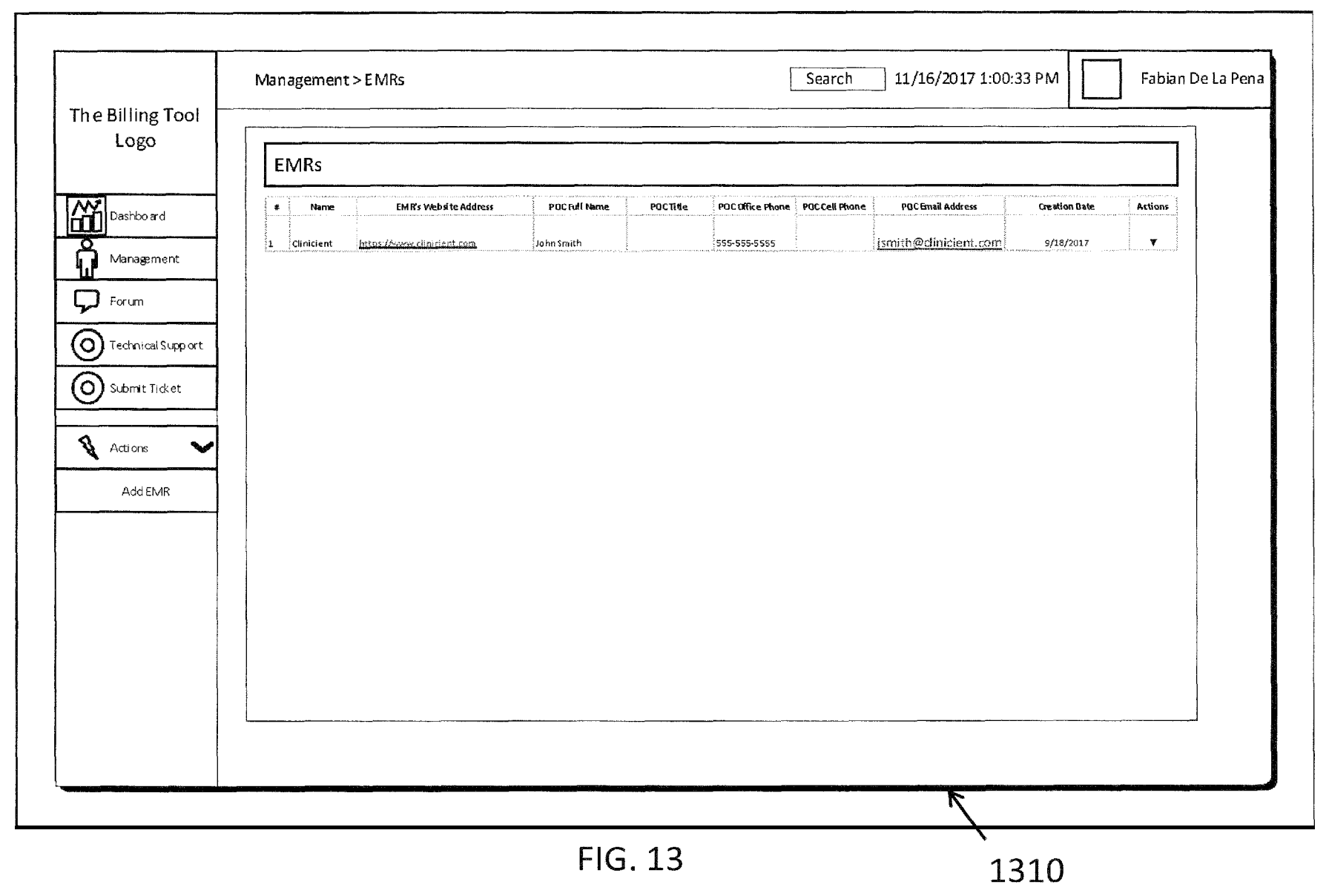

FIG. 13 shows the EMRs page 1310 that may be accessed by clicking on the EMRs button 1300 shown in FIG. 10. The EMRs page 1310 may provide information about one or more electronic medical record databases accessed by the billing application 112. For example, the EMRs page 1310 may include a list of EMR databases with claims, along with the EMR name, an EMR number, contact information for a point of contact with the EMR, and the date the EMR was added to the system. The list of EMR databases may be organized according to any of those categories. The EMRs page 1310 may include an "action" column to allow a managing user to annotate an entry, edit the information, or create a new entry.

FIG. 14 shows the provider specialties page 1410 that may be accessed by clicking on the Provider Specialties button 1400 shown in FIG. 10. The provider specialties page 1410 may provide information about the specialties of the clients with claims in the billing application 112. For example, the provider specialties page 1410 may list common specialties such as orthopedics, neurology, sports medicine, geriatrics, women's health, pediatrics, clinical electrophysiology, cardiovascular/pulmonary, and the like. The provider specialties page 1410 may include an "action" column to allow a managing user to annotate an entry, edit the information, or create a new entry.

FIG. 15A shows the worklists templates page 1510 that may be accessed by clicking on the Worklists Templates button 1500 shown in FIG. 10. The worklists templates page 1510 may provide information about the worklists within the billing application 112. Worklists are a prioritized list of patients for a biller to work through. The contents of a worklist may be displayed one patient at a time within the biller view. The worklist page shown in FIG. 15A is an interface where the manager can make changes to the prioritization schedule. The prioritization may be determined by a user of the manager view dashboard and may be displayed on at least one of the billing view dashboards in accordance with FIGS. 4-8, below. The manager user of the manager view dashboard may use the worklists templates page 1510 to create or edit the prioritization as described below. The system may, automatically or upon command from the user, update the prioritization shown in the billing view dashboard of the billing view user. The prioritization created by the manager user may create a new set of data corresponding to the claim information and insurance information collected and retrieved by the system. The new set of data may be the prioritized data that defines a worklist. In this way, the system may convert non-prioritized data into a standard prioritized dataset viewable by biller users of the system.

Figure 15B:
Figure 15C:
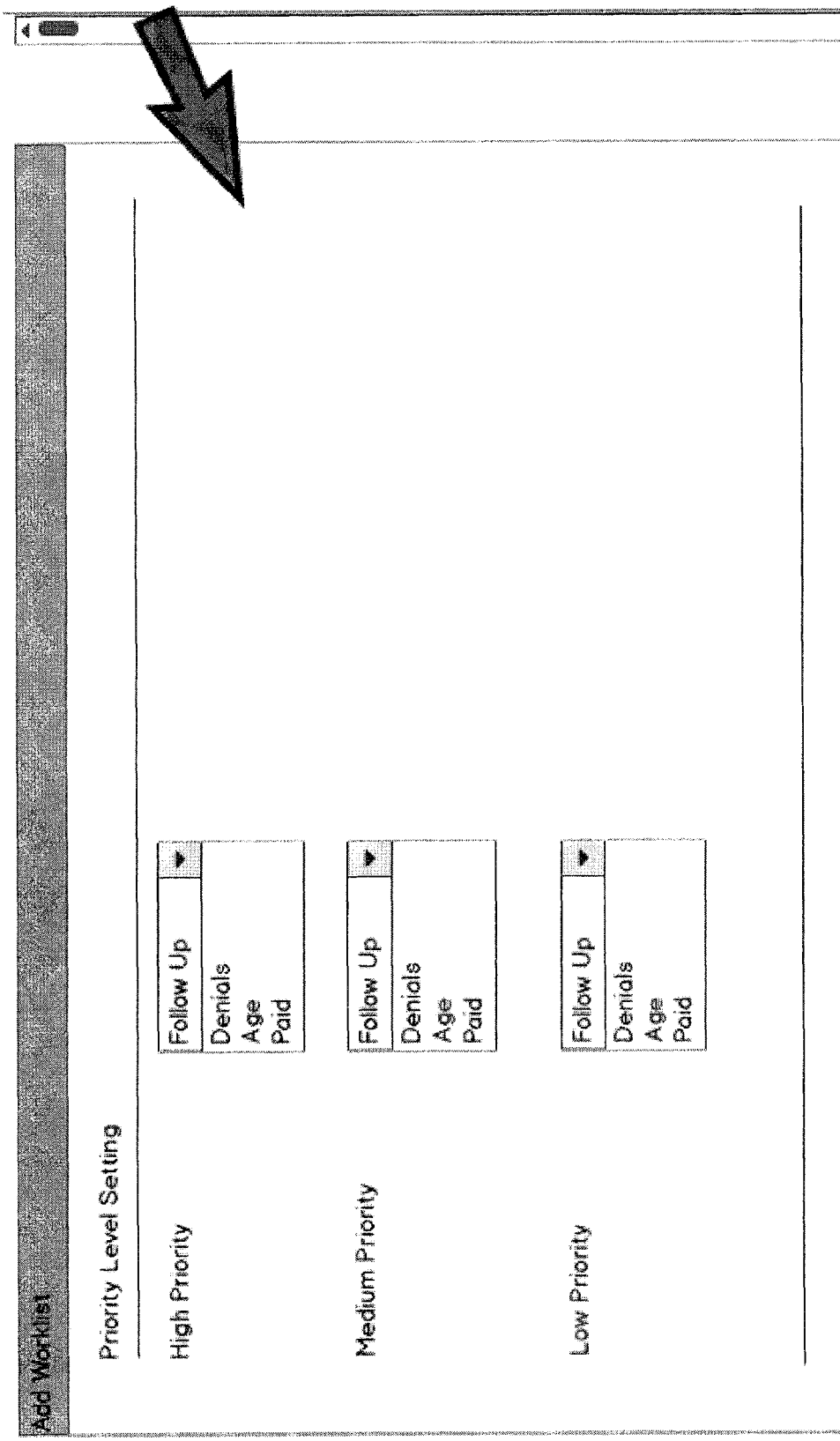

FIGS. 15B-D show worklist editing menus 1520 of the worklists templates page 1510 (FIG. 15A), in accordance with the first exemplary embodiment of the present disclosure. The worklist editing menu 1520 may allow a manager to create or edit a worklist according to desired criteria, which may include priority level, payer type priority, client priority, payer category priority, and payer priority, all of which may include a specific constraint type setting. As shown in FIG. 15B, the worklist editing menu 1520 may provide form entry menus, dropdown menus, and the like. By way of example, a manager may enter a worklist name, a priority template to use in the worklist, and a number of priority level settings. As shown in FIG. 15C, characteristic categories can be chosen for the priority level settings. Categories may be selected for high priority, medium priority, and low priority levels. As shown in FIG. 15D, once categories are selected for each of the priority levels, additional filter options may become available. By way of example, if the category "Denials" is designated as high priority, the user may be able to specify a narrower type of denial on which the application can focus, which may include, for example, denials that are new, denials based on electronic medical records (EMR), website denials, or others. If the category "Age" is designated as medium priority, the user may be able to specify an age range to apply the priority over. Categories may allow for further specification regardless of the priority level selected. Returning to FIG. 15B, after the priority level settings have been chosen, the user may select further options such as payer type priority and constraint type, client priority, payer category priority and constraint type, payer priority and constraint type, and the like.

Figure 16:
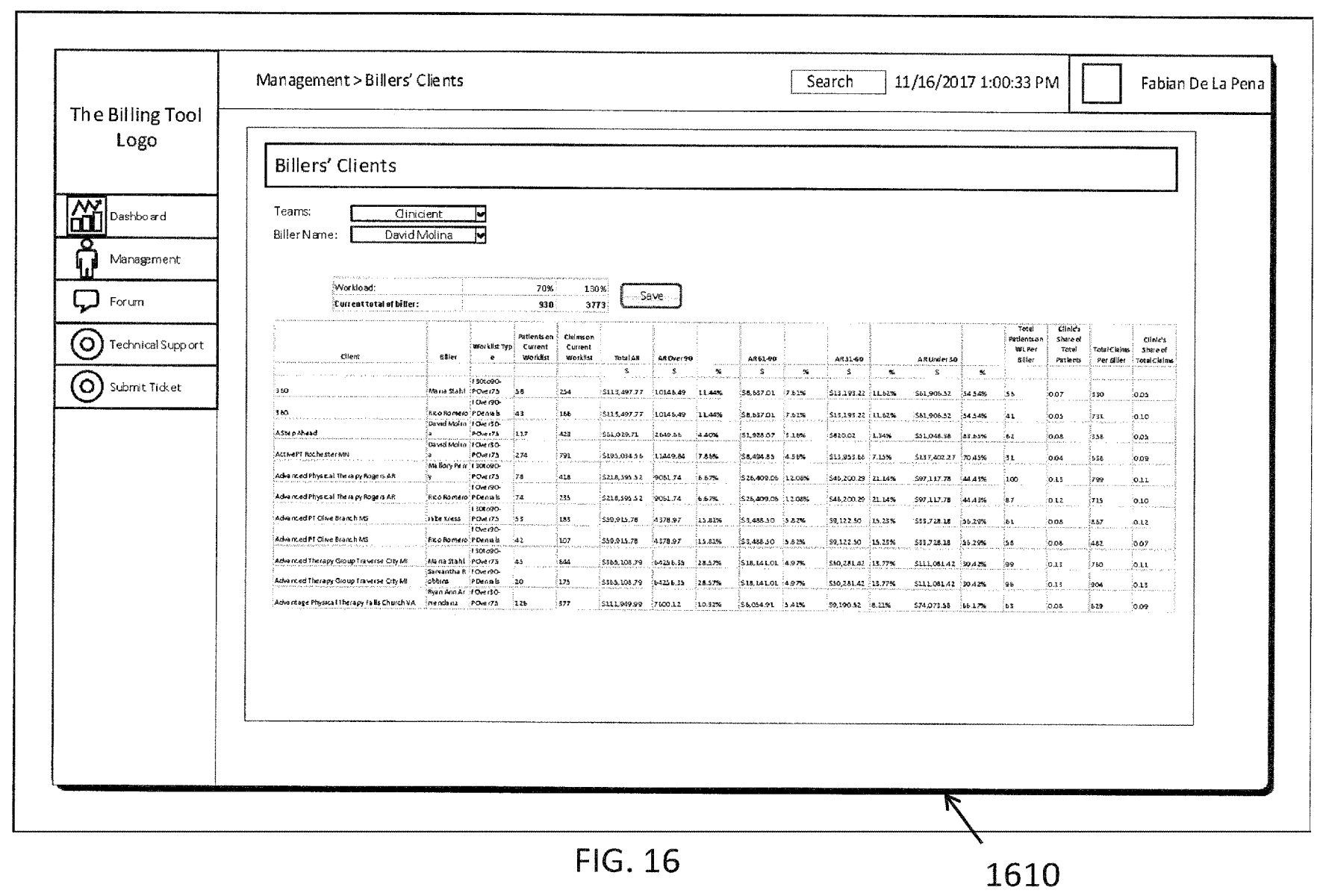

FIG. 16 shows the billers' clients page 1610 that may be accessed by clicking on the Billers' Clients button 1600 shown in FIG. 10. The billers' clients page 1610 may provide information about which clients each biller is working with. By way of example, FIG. 16 shows a list of 7 clients, along with the names of billers working on their claims, the type of worklist the billers are utilizing, the number of patients on the worklist, the number of claims on the worklist, amounts in several categories of accounts receivable, and information on the clients' work as a portion of total work. Other information may also be included. The billers' clients page 1610 may allow a managing user to organize the list by any of these categories.

FIG. 17 shows the billers page 1710 that may be accessed by clicking on the Billers button 1700 shown in FIG. 10. The billers page 1710 may provide information about a particular biller's performance over time. The billers page may include identifying information about the biller, information relating to a target goal and progress toward that goal, and tables and graphs showing work performance over an amount of time, for instance per day, week, or month. A managing user may be able to set and reset target goals for the biller. The billers page 1710 may also allow a managing user to assign additional worklists or individual claims to the biller.

Figure 18:
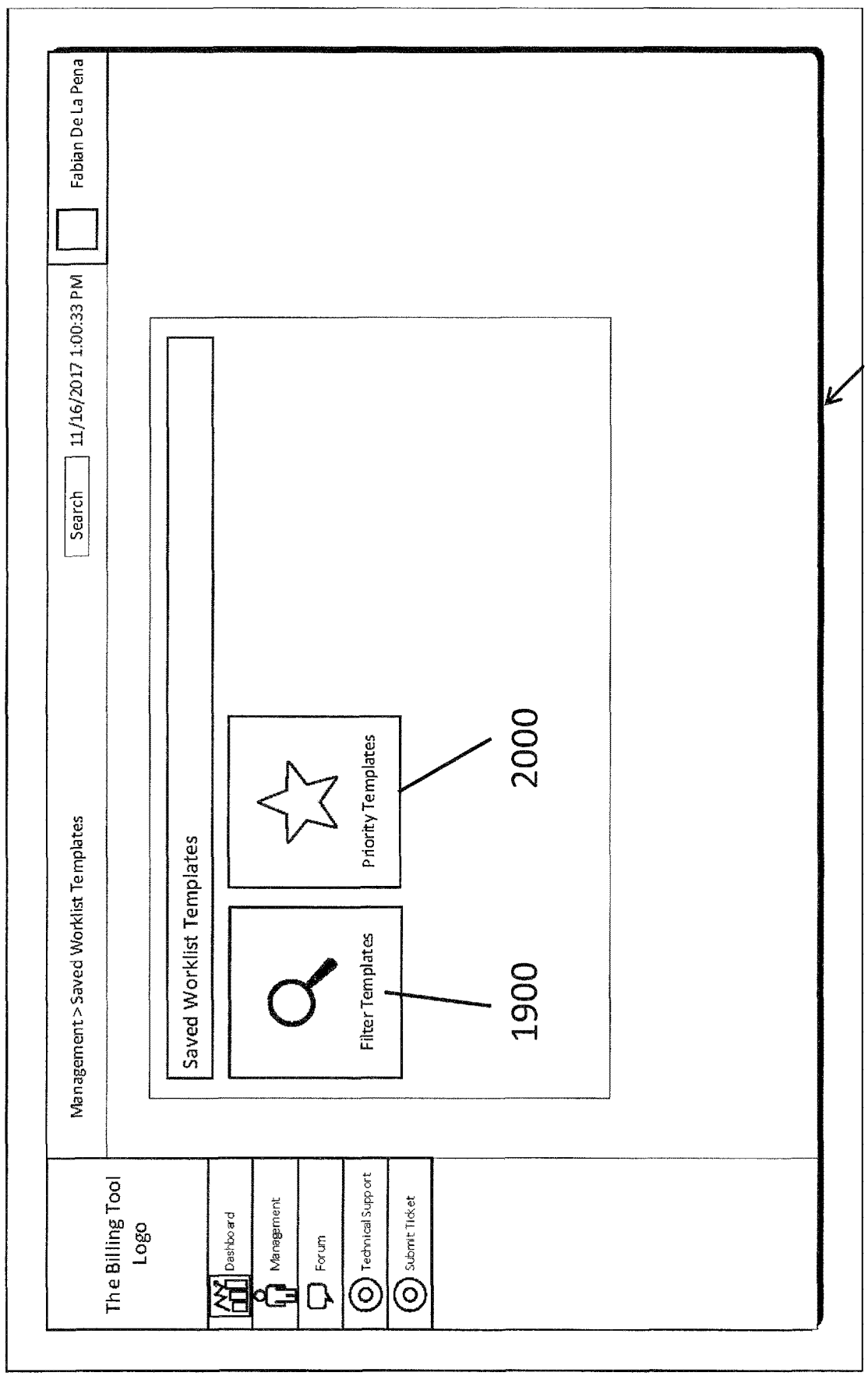
FIG. 18 shows a saved worklists templates page of the billing application, in accordance with the first exemplary embodiment of the present disclosure.

FIG. 18 shows the saved worklists templates page 1810 that may be accessed by clicking on the Saved Worklists Templates button 1800 shown in FIG. 10. The saved worklists templates page 1810 may include navigational buttons 1900, 2000 comprising graphics, text, or a combination thereof. The Filter Templates button 1900 and the Priority Templates button 2000 direct users to additional pages discussed in FIGS. 19-20, below.

Figure 19:
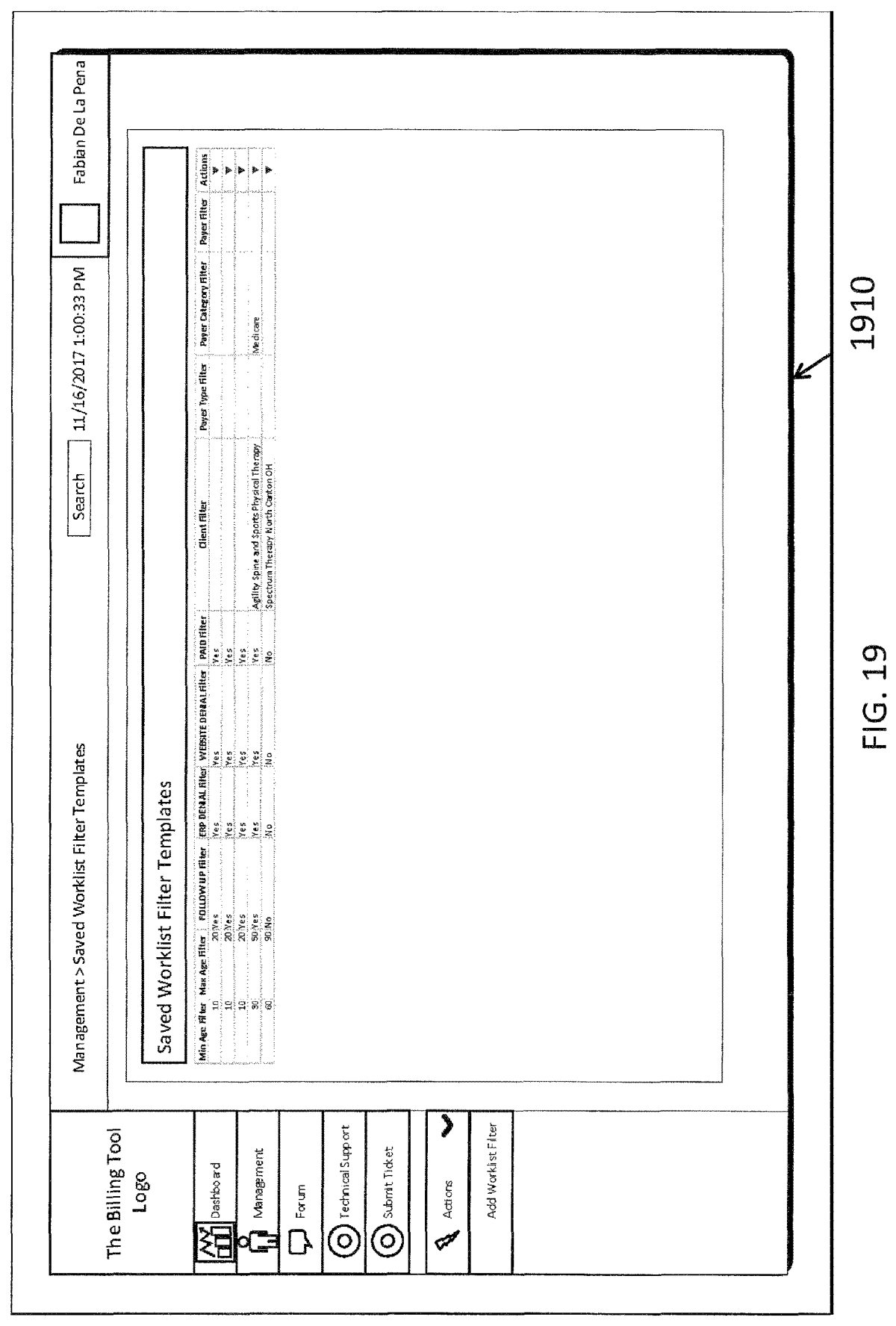

FIG. 19 shows the filter templates page 1910 that may be accessed by clicking on the Filter Templates button 1900 shown in FIG. 18. The filter templates page 1910 shows saved filter templates within the system that a manager can access. The filter templates may be used by the manager to create boundaries, such as starting points and ending points, for the prioritization schedule. Filter templates may include filters based on claim age data, claim balance data, payer data, status data, provider data, CPT code data, and action code data. The retrieved insurance claim data may be filtered according to at least one of these data fields. For example, the manager may want the worklist to only contain claims that are greater than a certain age, such as 30 days old. Filtering by claim balance data may include excluding claims with claim balances outside of a desired range from a worklist. For example, claims with claim balances beneath a threshold may be filtered. Filtering by payer data may include excluding claims directed to particular insurance provider payers. Filtering by status data may include excluding claims with a particular status, for example, claims being processed, new claims, and the like. Filtering by provider data may include excluding claims originating from particular medical service providers. Filtering by CPT code data may include excluding particular CPT codes or ranges of codes. As a corollary, filtering by exclusion of claims with particular data field values may be performed by including only claims with particular data field values. Thus, filtering claims by age data may involve removing claims outside of a given age range or including claims within a given age range. Both inclusive and exclusive filtering are contemplated within the scope of this disclosure. The manager may select a filter that narrows the list of total claims down to a smaller list of claims the manager would then like to prioritize. This is discussed in greater detail in the priority examples below. In another example, filter templates may be enacted automatically by the system. For instance, the system may enact a filter template at periodic dates, such as the beginning or the end of fiscal calendars. In one example, the system may monitor the retrieved and collected data and may automatically set filters based on the characteristics of the associated claims. For instance, if a large number of high-value claims are pulled on a particular date, the system may automatically filter out lower value claims when the high-value claims are nearing an unrecoverable age.

Figure 20:
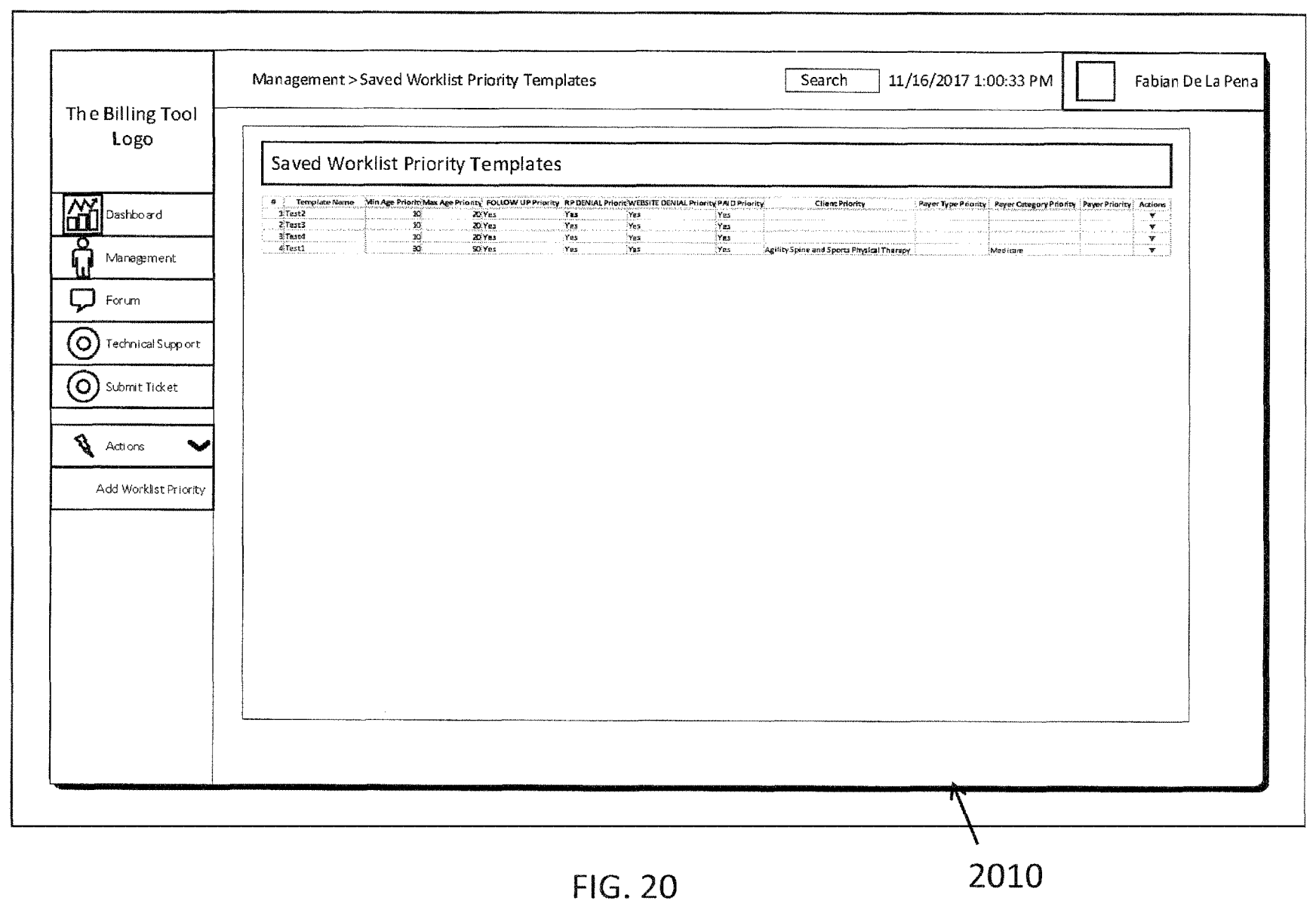

FIG. 20 shows the priority templates page 2010 that may be accessed by clicking on the Priority Templates button 2000 shown in FIG. 18. The priority templates page 2010 may display saved priority filters within the system that a manager can access. The priority filters allow the manager to apply priorities to various measures such as balance, claim age, claim status, previous follow-up, and the like. By selecting a high, medium, or low priority, a multiplier may be applied to the claims which causes the claims to move higher or lower on the list accordingly. For example, by choosing claim age as the highest priority, a large multiple is applied to older claims, which makes these claims appear higher on the list even if they have lower balances than newer claims. In another example, by choosing previous follow-up as the highest priority, claims that have not previously been followed-up on will appear higher than other claims of the same value that have been followed-up on. This is discussed in greater detail in the priority examples below.

Figure 21:
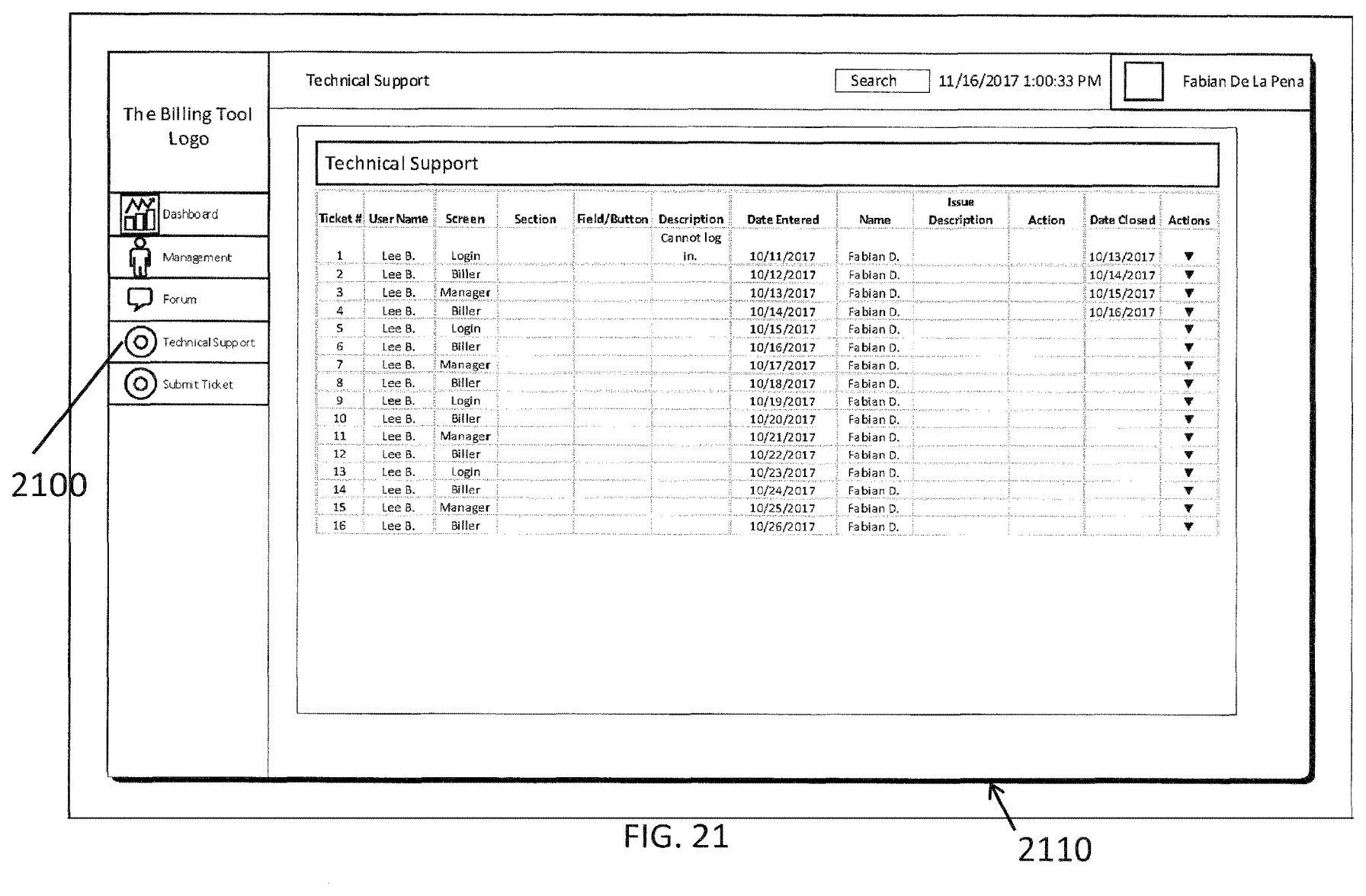

FIG. 21 shows the technical support page 2110 that may be accessed by clicking on the Technical Support button 2100. The technical support page 2110 may provide error and bug information submitted by users of the billing application 112 to allow managing users and developers to monitor and update the billing application 112. The information may include a support ticket number, the name of the biller who reported the error, the circumstances surrounding the error, and any actions taken to work around the error, among others. The technical support page 2110 may also include an "action" button that allows a user to edit or annotate an existing entry.

PRIORITY EXAMPLES

The following priority examples may illustrate how the filters and priority filters can be implemented to create prioritized worklists. In the priority examples, characteristic categories may be indicated as high priority, medium priority, or low priority. Each priority level corresponds to a multiplier assigned to an aspect of the claim. Low priority categories may receive a small multiplier, such as 1. Medium priority categories may receive a larger multiplier, such as 2. High priority categories may receive a still higher multiplier, such as 3. These values are exemplary and may be different depending on the implementation of the application. The priority examples may also contain high-level examples of code that can be adapted into the application to achieve the priority filters.

At least one multiplier may be applied to at least a portion of the medical claim data. For example, one multiplier may be applied to a claim balance of a medical claim in order to determine a standardized value of the claim. In this way, the standardized monetary value of all claims within a list may be determined, and a biller may work through the list according to a prioritization directed to the highest value claims first. As another example, one multiplier may be applied to a claim age of a medical claim in order to create a standardized age value of the claim. In this way, the standardized value of all claims within a list may be determined, and a biller may work through the list according to a prioritization of the highest value claims first. This may be desirable if a biller is required to process a certain number or type of claims within a particular amount of time. One multiplier may be applied to any of the data fields of the medical claim information in order to create standardized values for these claims relative to a particular field. Additionally, more than one multiplier may be applied to a single data field of a medical claim. In one example, the multipliers may be determined based on different data fields, such as age, provider, and status. The multipliers may then be applied to a single data field, such as claim balance, in order to create a standardized value of the medical claim that can be prioritized as described above. For instance, multipliers may be determined based on a claim's age and medical service provider, then applied to the claim balance to create a standardized monetary value of the claim. This may be done for each claim in a worklist to deter nine the highest value claims based on a hierarchy of multiple priorities. In one example, every data field corresponding to a claim may be assigned a multiplier, and every multiplier may be applied to one or more data fields in order to determine a standardized value for prioritization. The examples below discuss this in detail.

The prioritization may be determined by a hierarchy of at least one of the data fields corresponding to the medical claim. As an example, where the data fields of a medical claim include claim age, claim balance, payer, status, provider, CPT code, and action code, the data fields may be arranged according to a hierarchy of importance. For instance, claim balance may be of highest importance, followed by claim age, followed by claim status, and so on. The hierarchy may depend on performance metrics desired by the biller. For example, a biller may have a requirement to process a certain monetary value, a certain number of claims, a certain type of claims, and so on. Therefore, the hierarchy may be arranged according to these requirements. The prioritization of claims in a worklist may be determined according to this hierarchy as applied to the multipliers.

Example 1

In the first example, the high priority level is set to a "Denial" category, while the medium and low priority levels are left blank. The application applies a multiplier of 3 to the dollar amount of any claims having a denial status, and then reorganizes the worklist based on the claims with the highest dollar amount.

```
IF      "High Priority" = 'Denial'
        "Medium Priority" = 'None'
        "Low Priority" = 'None'
THEN
        Dollar amount of claims with status 'Denial'
should be multiplied by 3
```

Example 2

In the second example, the high priority level is set to a "Follow Up" category, while the medium and low priority levels are left blank. The application applies a multiplier of 3 to the dollar amount of any claims having a follow up status, and then reorganizes the worklist based on the claims with the highest dollar amount.

```
IF      "High Priority" = 'Follow Up'
        "Medium Priority" = 'None'
        "Low Priority" = 'None'
THEN
        Dollar amount of claims with status 'Follow Up'
should be multiplied by 3
```

Example 3

In the third example, the high priority level is set to an "Age" category, while the medium and low priority levels are left blank. The application applies a multiplier to the dollar amount of the claim based on its age; older claims are given a higher multiplier, while newer claims are given a lower multiplier. The application then reorganizes the worklist based on the claims with the highest dollar amount.

```
IF      "High Priority" = 'Age'
        "Medium Priority" = 'None'
        "Low Priority" = 'None'
THEN
        Dollar amount of claims should be multiplied as
per below age condition:
High    31-60           1.75    used
        61-90           2       used
        91-120          2.25    used
        121 and         2.5     used
        older
```

If the manager has also applied an age range filter, the application first checks to determine whether the claim falls in the allowable age range before applying the multiplier. For example, if a filter only allows claims between 61 days and 120 days, then the result would be the following:

```
IF      "High Priority" = 'Age'
        "Medium Priority" = 'None'
        "Low Priority" = 'None'
THEN
        Dollar amount of claims should be multiplied as
per below age condition:
High    31-60           1.75    Not used because of
                                filtering condition
        61-90           2       used because of filtering
                                condition
        91-120          2.25    used because of
                                filtering condition
        121 and         2.5     Not used because of
        older                   filtering condition
```

Example 4

In the fourth example, the high priority level is set to a "Denial" category, the medium priority level is set to an "Age" category, and the low priority level is set to a "Follow Up" category. The application first applies a multiplier of 3 to the dollar amount of any claims with a denial status, then applies a variable multiplier to the dollar amount of all claims according to their age, then applies a multiplier of 1.5 to the dollar amount of any claims with a follow up status. This may result in some claims receiving a multiplier for each priority level. The application then reorganizes the worklist based on the claims with the highest dollar amount.

```
IF      "High Priority" = 'Denial'
        "Medium Priority" = 'Age'
        "Low Priority" = 'Follow Up'
THEN
        Step1: dollar amount of claims with status
'Denial' should be multiplied by 3
        Step2: dollar amount of claims should be
multiplied by the age parameter as mentioned below:
Medium  31-60           1.5     used
        61-90           1.75    used
        91-120          2       used
        121 and         2.25    used
        older
```

Note that if there is a claim with status denial, age 95 days and dollar amount of $100, then in the first step as per high priority condition, its dollar amount will become $100*3=$300. In the next step, as per the medium priority condition, its dollar amount will become $300*2=$600.

Step 3: dollar amount of claims with status 'Follow Up' should be multiplied by 1.5

If the manager has also applied an age range filter, the application first checks to determine whether the claim falls in the allowable age range before applying the multiplier. For example, if a filter only allows claims between 61 days and 120 days, then the result would be the following:

```
       IF       "High Priority" = 'Denial'
                "Medium Priority" = 'Age'
                "Low Priority" = 'Follow Up'
       THEN
                Step1: dollar amount of claims with status
'Denial' should be multiplied by 3
                Step2: dollar amount of claims should be
multiplied by the age parameter as mentioned below:
Medium      31-60       1.5         not used
            61-90       1.75        used
            91-120      2           used
            121 and     2.25        Not used
            older
```

Note that if there is a claim with denial status, age 95 days and dollar amount of $100, then in the first step as per high priority condition its dollar amount will become $100*3=$300. In the next step, as per the medium priority condition, its dollar amount will become $300*2=$600.

Step 3: dollar amount of claims with status 'Follow Up' should be multiplied by 1.5

Example 5

In the fifth example, the high priority level is set to a "Denial" category, the medium priority level is set to a "Follow Up" category, and the low priority level is set to "Age." The application first applies a multiplier of 3 to the dollar amount of any claims with a denial status, then applies a multiplier of 2 to the dollar amount of any claims with a follow up status, then applies a variable multiplier to the dollar amount of claims based on their age. The application then reorganizes the worklist based on the claims with the highest dollar amount.

```
       IF       "High Priority" = 'Denial'
                "Medium Priority" = 'Follow Up'
                "Low Priority" = 'Age'
       THEN
                Step1: dollar amount of claims with status
'Denial' should be multiplied by 3
                Step2: dollar amount of claims with status
'Follow Up' should be multiplied by 2
                Step 3: dollar amount of claims should be multiplied
by the age parameter as mentioned below:
Low         31-60       1.15        Used
            61-90       1.25        Used
            91-120      1.5         Used
            121 and     1.75        Used
            older
```

Note that if there is a claim with status denial, age 95 days and dollar amount of $100 then in the first step as per high priority condition it's dollar amount will become $100*3=$300. In the third step, as per the low priority condition, its dollar amount will become $300*1.5=$450. For example, if there is a claim with status follow up, age 95 days and dollar amount of $100 then in the second step as per medium priority condition it's dollar amount will become $100*2=$200. In the third step, as per the low priority condition, its dollar amount will become $200*1.5=$300.

If the manager has also applied an age range filter, the application first checks to determine whether the claim falls in the allowable age range before applying the multiplier. For example, if a filter only allows claims between 61 days and 120 days, then the result would be the following:

```
       IF       "High Priority" = 'Denial' (or Follow Up)
                "Medium Priority" = 'Follow Up' (or Denial)
                "Low Priority" = 'Age'
       THEN
                Step1: dollar amount of claims with status
'Denial' should be multiplied by 3
                Step2: dollar amount of claims with status
'Follow Up' should be multiplied by 2
Step 3: dollar amount of claims should be multiplied
by the age parameter as mentioned below:
Low         31-60       1.15        Not Used
            61-90       1.25        Used
            91-120      1.5         Used
            121 and     1.75        Not Used
            older
```

Note e.g. if there is a claim with status denial, age 95 days and dollar amount of $100 then in the first step as per high priority condition it's dollar amount will become $100*3=$300. In the third step, as per the low priority condition, its dollar amount will become $300*1.5=$450. For example, if there is a claim with status follow up, age 95 days and dollar amount of $100, then in the second step as per medium priority condition it's dollar amount will become $100*2=$200. In the third step, as per the low priority condition, its dollar amount will become $200*1.5=$300.

Example 6

In the sixth example, the high priority level is set to a "Denial" category, the medium priority level is set to a "Follow Up" category, and the low priority level is left blank. The application first applies a multiplier of 3 to the dollar amount of any claims with a denial status, then applies a multiplier of 2 to the dollar amount of any claims with a follow up status. The application then reorganizes the worklist based on the claims with the highest dollar amount.

```
       IF       "High Priority" = 'Denial'
                "Medium Priority" = 'Follow Up'
                "Low Priority" = 'None'
       THEN
                Step1: dollar amount of claims with status
'Denial' should be multiplied by 3
                Step2: dollar amount of claims with status
'Follow Up' should be multiplied by 2
```

If the manager has also applied an age range filter, the application first checks to determine whether the claim falls in the allowable age range before applying the multiplier. For example, if a filter only allows claims between 61 days and 120 days, then the result would be the following:

```
       IF       "High Priority" = 'Denial'
                "Medium Priority" = 'Follow Up'
                "Low Priority" = 'None'
       THEN
                Step1: dollar amount of claims with status
                'Denial' and age between 61
days to 120 days should be multiplied by 3
                Step2: dollar amount of claims with status
'Follow Up' and age between 61 days to 120 days should
be multiplied by 2
```

Figure 22:
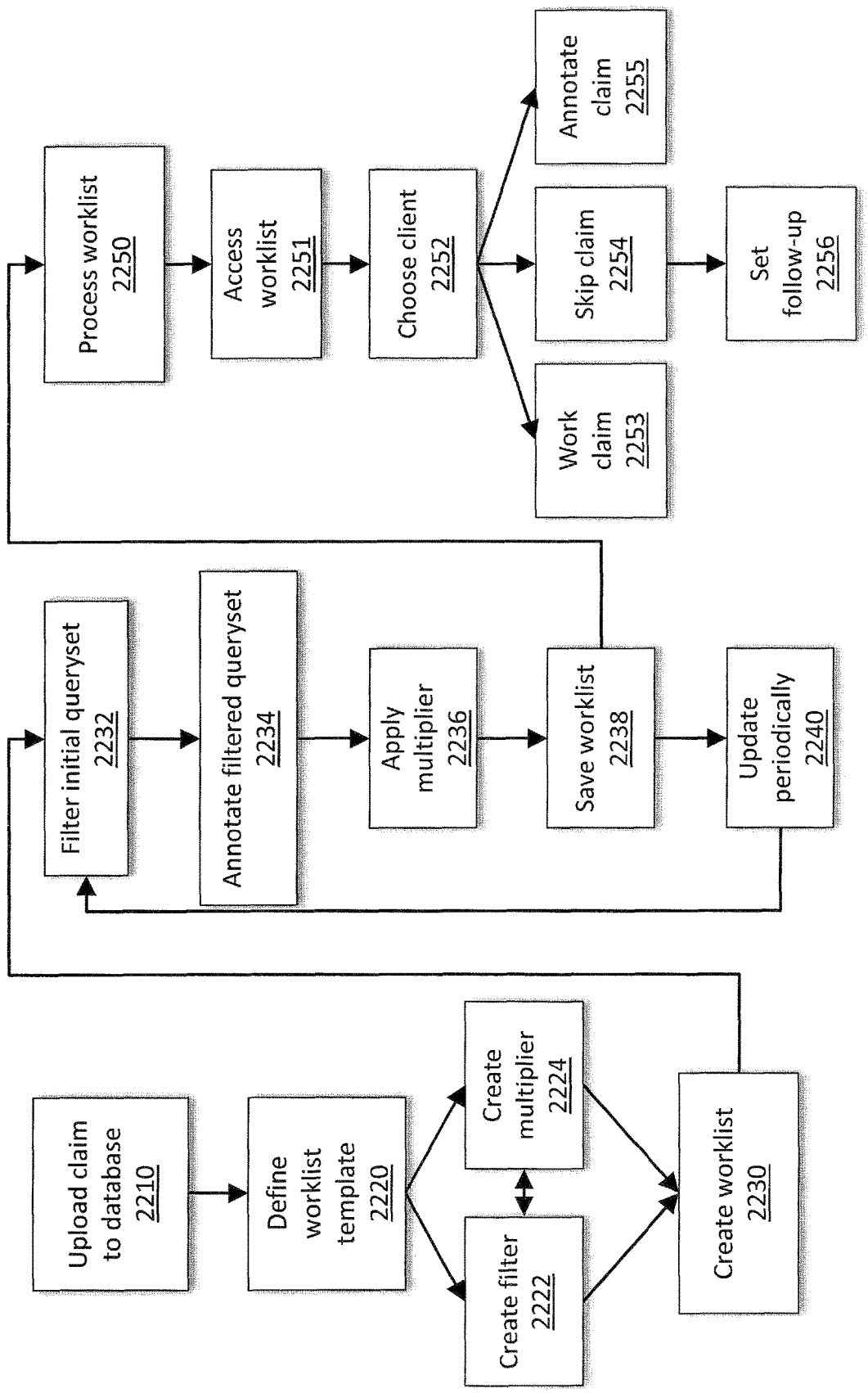
FIG. 22 is a flow chart illustrating an exemplary implementation of the method for medical claims billing management, in accordance with the second exemplary embodiment of the present disclosure.

FIG. 22 is a flow chart illustrating an exemplary implementation of the method for medical claims billing management, in accordance with the second exemplary embodiment of the present disclosure. FIG. 22 shows a software implementation of the system and method described relative to FIGS. 1-21 and is exemplary in nature. Other software implementations may be considered within the scope of this disclosure.

Step 2210 includes uploading a claim to a database. The claim may be a dataset containing multi-field data corresponding to a medical service claim for billing. The data fields may include the claim balance value, a unique claim identifier, a patient identifier, a client identifier, an insurance payer identifier, a claim status, CPT codes, a claim date, and similar information. Each claim may have a plurality of data fields making up a single claim. Claims may be uploaded to a relational, subject-oriented database. Claims may also include information corresponding to insurance claims related to the medical service. Claims may be uploaded automatically by a software program, as discussed above.

Step 2220 includes defining a worklist template. This step, along with Steps 2222-2240, may be performed using the manager view dashboards discussed in FIGS. 9-21. The worklist template may be defined by creating a filter, as in Step 2222. The filter may exclude a number of claims from further processing based on the values of data in one or more fields. For example, a filter may exclude claims based on minimum or maximum ages, minimum or maximum claim balances, payer identity, claim status, medical provider, CPT codes, action codes, reasons for skipping, payer filters, or some combination thereof. In one example, a filter may be set to include claims having desired data field values rather than exclude claims. The worklist may also be defined by creating one or more multipliers that can be applied to values in one or more data fields. For example, the age of a claim may be an important consideration in deciding whether its handling is a priority. Claims having older age values may be given higher multipliers than claims having newer age values. More specifically, if a value in a data field, such as claim age, falls within a given range, it may be assigned one multiplier. If the value falls outside of the given range, it may be assigned another multiplier. The multiplier scheme may be determined by a user or by a software algorithm. Filters and multipliers may both be created and applied in any order desired.

Step 2230 includes creating a worklist for one or more billers. The worklist may be an assignment of one or more claims to the one or more billers in a particular order determined according to the worklist template defined in Step 2220. The worklist may consider the initial queryset, which may be all claims uploaded to the database in Step 2210 that are active and in need of processing. The initial queryset may be filtered in Step 2232 by applying the filter or filters created in Step 2222. Claims excluded by the filter are not considered for the remainder of the process, while claims that are included by the filter are further processed. The filtered queryset may be further filtered if, for example, claims are included that have a scheduled follow-up date at a point in the future. This is discussed further in Step 2256. Step 2234 includes annotating the filtered queryset with a new data field corresponding to a standardized value. The standardized value may be determined after the at least one multiplier is applied to the claim. The standardized value may be a value converted from one or more data field values and the at least one multiplier. In one example, the standardized value may represent a monetary value calculated from the claim balance and another field, such as the claim age. In another example, the standardized value may represent an age value calculated from the claim age and another field. Step 2236 includes applying the multiplier. This operation is discussed in detail relative to the priority examples above.

Step 2238 may include saving the worklist. This may include creating an order of the prioritization of all claims in the filtered queryset, for instance, from large to small according to the standardized value. Saving may include electronically recording the worklist in memory, as well as providing real-time access to the worklist to other biller users. The worklist may be updated periodically in Step 2240, wherein steps 2232-2238 may be performed again in order to update any time-sensitive filters or multipliers. As an example, the worklist may be updated daily, hourly, or quarter-hourly, depending on the implementation of the software method.

Step 2250 includes processing the worklist. A biller may access the worklist in Step 2251 after it has been provided and may process claims according to the order given by the worklist. This may be graphically displayed in the plurality of billing view dashboards described in FIGS. 3-8. In one example, a biller may choose a client as in Step 2252, meaning the biller may work on the claims for one client in particular at a time. Once the client has been chosen, the biller may be presented with one open claim to work at a time.

The biller may choose to process the claim in a number of ways. In Step 2253, the biller may work the claim by processing it with the payer insurance provider in an attempt to reach a successful billing result. In Step 2254, the biller may skip the claim and choose to work on another claim. When skipping a claim, the biller may choose to set a date at which to follow-up on the skipped claim, as shown in Step 2256. The follow-up date may indicate a date at which the skipped claim becomes a higher priority to be processed. In Step 2255, the biller may annotate the claim. This may include adding notation or textual descriptions to the metadata of the claim in order to document the biller's attempts to process the claim. For example, the annotation may indicate that the biller was successful, was unsuccessful, spoke with a particular representative, and so on. The biller may include action codes in the notation that indicate the preferred next step for processing the claim, such as electronic processing, telephone calls, escalation, and the like. The biller may work through all or a portion of the claims on the worklist in order to process all of the priority claims according to the standardized value determined by the software.

Figure 23:
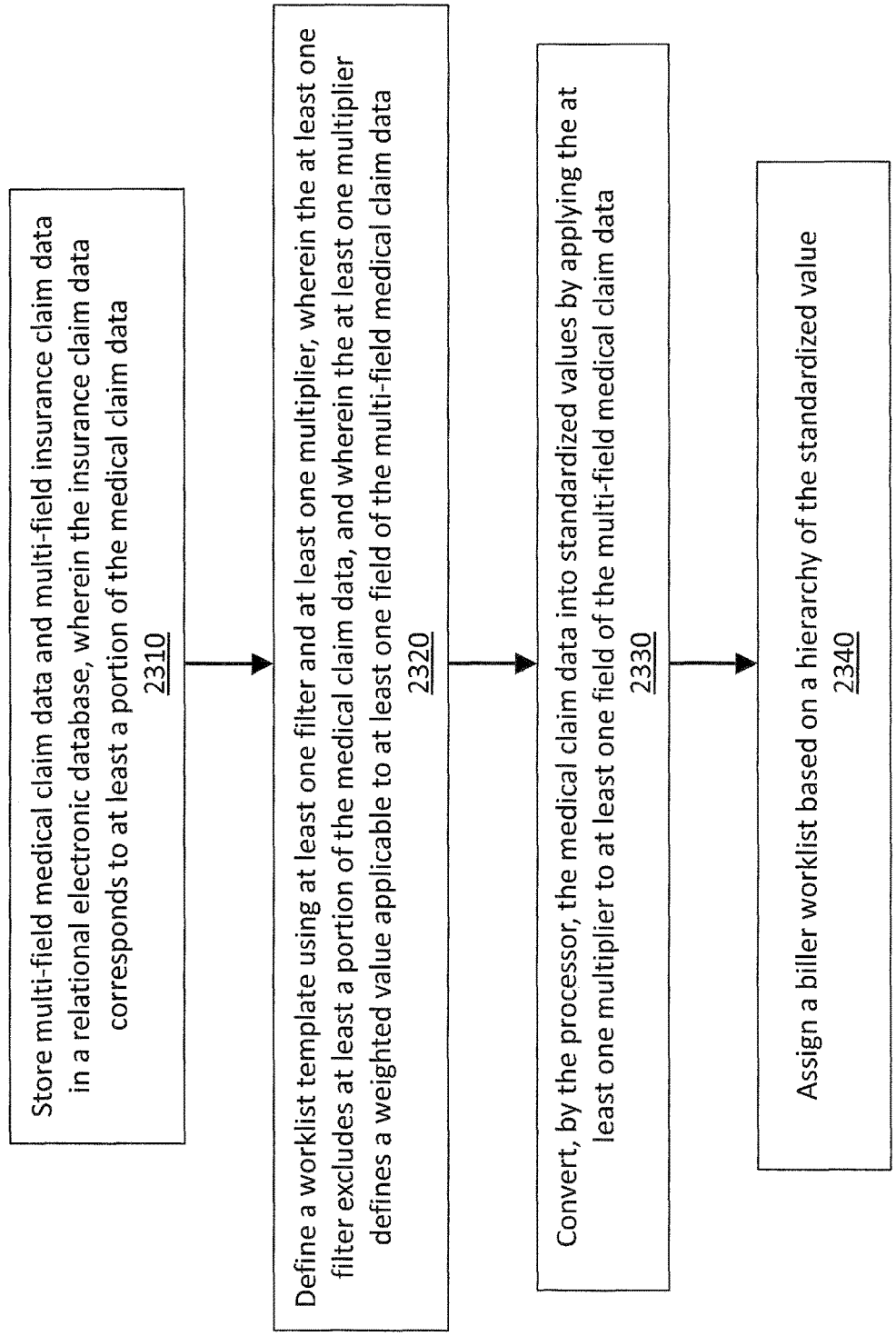
FIG. 23 is a flow chart illustrating a method for processing relationships in a medical claims database, in accordance with a third exemplary embodiment of the present disclosure.

FIG. 23 is a flow chart illustrating a method for processing relationships in a medical claims database, in accordance with a third exemplary embodiment of the present disclosure.

Step 2310 includes storing multi-field medical claim data and multi-field insurance claim data in a relational electronic database, wherein the insurance claim data corresponds to at least a portion of the medical claim data. The multi-field medical claim data and multi-field insurance claim data may be data corresponding to a claim for medical treatment as described above. The medical and insurance claim data may be stored in a relational electronic database by a software program. The software program may collect and retrieve the medical and insurance claim data from their respective websites or their respective databases as described above using web scraping, ODBC or an API. The medical and insurance claim data may be temporarily stored on the relational database to facilitate processing of the relationships within the multiple tiers, or it may be stored until the claim has been successfully processed.

Step 2320 includes defining a worklist template using at least one filter and at least one multiplier, wherein the at least one filter excludes at least a portion of the medical claim data, and wherein the at least one multiplier defines a weighted value applicable to at least one field of the multi-field medical claim data.

The filter may exclude at least a portion of the medical claim data. For example, the filter may exclude medical claims outside of a desired age range, balance value, or insurance payer. The filter may be used to narrow a list of claims to a smaller list for focused processing. The at least one multiplier may be a numerical value applied to weight at least one field of the multi-field medical claim data. As discussed relative to the priority examples above, the at least one multiplier may be determined based on a hierarchy of data field values and may be applied to one or more data field values of a list of claims.

A worklist template may be further defined using additional numerical processing. For instance, the medical claims corresponding to the medical and insurance claim data may be sorted according to the values of the data in one or more fields. In one example, the medical claims may be sorted according to claim balance, either by largest-to-smallest or smallest-to-largest order. Sorting by smallest-to-largest order may be done by applying a negative multiplier to the claim balances and sorting by largest-to-smallest. In another example, the worklist template may be definable based on a claim data field. The claim data field used to define the worklist template may be toggled by the user in practice, allowing the worklist template to be updateable.

Step 2330 includes converting, by the processor, the medical claim data into standardized values by applying the at least one multiplier to at least one field of the multi-field medical claim data. The processor may apply the at least one multiplier to the filtered list of medical claims by applying the at least one multiplier's numerical value to the numerical value of at least one field for each medical claim in the filtered list. This may create a standardized value of the claim with relation to the at least one field. For example, a multiplier may be applied to the claim balance of each claim in order to determine the standardized monetary value of each claim within the filter list. This may allow a user to process the claims according to a prioritization determined by the standardized value, i.e., by higher value claims first. As another example, a multiplier may be applied to the age of each claim within the filtered list to create a standardized age value of each claim. Multipliers of different weights may be applied to each claim according to a hierarchy determined by the user in order to create a standardized value with which to evaluate and process the medical claims. This may allow the relational claim data across multiple fields of a claim to be reconciled in a single value data point, thereby providing a value based on the relative weights of each data field.

Step 2340 includes assigning a biller worklist based on a hierarchy of the standardized value. After the processor has applied the multiplier to each of the claims and the total number of claims has been filtered, the processor may assign a biller worklist based on a hierarchy of the standardized value of each claim. For example, a standardized balance value may have been created for each claim in the filtered list. The processor may assign a worklist to a biller based on a hierarchical order, such as largest balance to smallest, of each claim. This worklist may create a priority schedule from which a biller may work to process the claims within the filtered list. Multiple standardized balances may be created for each claim in the filtered claim worklist. The claims may be ordered according to the hierarchy. For example, high balance claims may be ordered first, and within that, the oldest claims may be ordered before the newest claims. The hierarchy may be determined by a managing user or by a software algorithm to maximize an aspect of medical claims processing such as monetary value collected, number of claims processed, average processing time, and the like.

It should be emphasized that the above-described embodiments of the present disclosure, particularly, any "preferred" embodiments, are merely possible examples of implementations, merely set forth for a clear understanding of the principles of the disclosure. Many variations and modifications may be made to the above-described embodiment(s) of the disclosure without departing substantially from the spirit and principles of the disclosure. All such modifications and variations are intended to be included herein within the scope of this disclosure and the present disclosure and protected by the following claims.

What is claimed is:

1. A method for processing data relationships in a remote medical and insurance claim database using a computerized system having a processor and a non-transitory memory, the method comprising:

storing multi-field medical claim data and multi-field insurance claim data in a relational electronic database, the medical claim data and insurance claim data remotely retrieved over an electronic network system, wherein the insurance claim data corresponds to at least a portion of the medical claim data;

defining an electronic worklist template using at least one filter and at least one multiplier, wherein the at least one filter excludes at least a portion of the medical claim data, and wherein the at least one multiplier defines a weighted value applicable to at least one field of the multi-field medical claim data;

converting, by the processor, the medical claim data into standardized values by applying the at least one multiplier to at least one field of the multi-field medical claim data to generate a single value point for each medical claim data entry;

automatically generating, on a display screen of a user computer device, an interactive worklist dashboard having a viewable biller worklist based on a hierarchy of the standardized values; and visually displaying the viewable biller worklist on the display screen of the user computing device, wherein a single medical claim data entry from the viewable biller worklist is displayed at a given time, and in a prioritized order from most valuable entry to least valuable entry relative to all medical claim data entries.

2. The method of claim 1, wherein at least one multiplier is applied to one of: a claim balance and a claim age of the medical claim data.

3. A method for data processing of remotely-collected medical claims billing data using a computerized system having a processor and a non-transitory memory, the method comprising:

electronically collecting, on a server, multi-field medical claim data from a relational, subject-oriented electronic medical records (EMR) database of a medical provider, wherein the relational subject-oriented EMR database is located remote from the server and wherein the medical claim data is collected over at least one electronic network system;

electronically retrieving, by the server, multi-field insurance claim data from a remote insurance database, wherein the insurance claim data corresponds to at least a portion of the medical claim data, wherein the remote insurance database is located remote from both the relational subject-oriented EMR database and the server, and wherein the insurance claim data is retrieved over the at least one electronic network system; and providing a plurality of visual dashboards on a computerized graphical user interface of a plurality of user computers connected to the server for viewing the collected medical claim data and the retrieved insurance claim data, each of the plurality of visual dashboards viewable and interactable by a user, wherein the plurality of dashboards comprises at least:

a plurality of billing view dashboards, each providing a viewable, visual indicator of prioritization of a handling of a portion of the medical claim data to a plurality of medical claim analysts, wherein the medical claim analysts communicate with an insurance provider associated with the portion of the medical claims data according to a schedule determined by the viewable, visual prioritization; and at least one manager view dashboard providing viewable, visual workflow information corresponding to the plurality of billing view dashboards for each of the plurality of user computers used by the medical claim analysts.

4. The method of claim 3, wherein the insurance claim data is retrieved using at least one from the set of: web scraping, an open database connectivity interface, or an application programming interface.

5. The method of claim 3, wherein the EMR database is a distributed database.

6. The method of claim 3, further comprising the step of filtering the retrieved insurance claim data according to at least one from the set of: a claim age, a claim balance, a payer, a status, a provider, a CPT code, and an action code.

7. The method of claim 3, wherein the prioritization is determined by applying at least one multiplier to at least a portion of the medical claim data.

8. The method of claim 7, wherein the at least one multiplier is applied to a claim balance of the medical claim data to create a standardized value of the medical claim data.

9. The method of claim 7, wherein the at least one multiplier is applied to a claim age of the medical claim data to create a standardized value of the medical claim data.

10. The method of claim 7, wherein the prioritization is determined by a hierarchy of at least one from the set of: a claim age, a claim balance, a payer, a status, a provider, a CPT code, and an action code.

11. The method of claim 3, wherein the prioritization is determined by a user of the at least one manager view dashboard and is displayed on at least one of the plurality of billing view dashboards.

12. A system for processing remotely-collected medical claims billing data, comprising:

a plurality of billing computer devices having a processor and non-transitory computer-readable memory;

a relational, subject-oriented electronic medical records (EMR) database of a medical provider containing multi-field medical claim data;

a remote insurance database containing multi-field insurance claim data corresponding to at least a portion of the medical claim data;

a server having a processor and non-transitory computer-readable memory, the server accessible over at least one network system by the billing computer device, the EMR database, and the insurance database, wherein the relational, subject-oriented EMR database and the remote insurance database are located remote from the server and the at least one billing computer device; and a billing management application running at least partially on the server, wherein the billing management application:

collects multi-field medical claim data from the relational, subject-oriented EMR database over the at least one network system;

retrieves multi-field insurance claim data from the insurance database over the at least one network system;

provides a plurality of visual dashboards on a computerized graphical user interface of the plurality of billing computer devices for viewing and interacting with the collected medical claim data and the retrieved insurance claim data, wherein each of the plurality of dashboards provides a viewable, visual indicator of prioritization of a handling of a portion of the medical claims data to a plurality of medical claim analysts, wherein the medical claim analysts communicate with an insurance provider associated with the portion of the medical claims data according to a schedule determined by the viewable, visual prioritization; and provides at least one manager view dashboard providing viewable, visual workflow data corresponding to the plurality of billing view dashboards for each of the plurality of billing computer devices used by the medical claim analysts.

13. The system of claim 12, wherein the insurance claim data is retrieved using at least one from the set of: web scraping, an open database connectivity interface, or an application programming interface.

14. The system of claim 12, wherein the EMR database is a distributed database.

15. The system of claim 12, wherein the retrieved insurance claim data is filtered according to at least one from the set of: a claim age, a claim balance, a payer, a status, a provider, a CPT code, and an action code.

16. The system of claim 12, wherein the prioritization is determined by applying at least one multiplier to at least a portion of the medical claim data.

17. The system of claim 16, wherein the at least one multiplier is applied to a dollar value of the medical claim data to create a standardized value of the medical claim data.

18. The system of claim 16, wherein the at least one multiplier is applied to a claim age of the medical claim data to create a standardized value of the medical claim data.

19. The system of claim 16, wherein the prioritization is determined by a hierarchy of at least one from the set of: a claim age, a claim balance, a payer, a status, a provider, a CPT code, and an action code.

20. The system of claim 12, wherein the prioritization is determined by a user of the at least one manager view dashboard and is displayed on at least one of the plurality of billing view dashboards.

* * * * *